(12) United States Patent
Jochumsen et al.

(10) Patent No.: US 12,016,536 B2
(45) Date of Patent: Jun. 25, 2024

(54) ENDOSCOPE TIP PART

(71) Applicant: AMBU A/S, Ballerup (DK)

(72) Inventors: Hans Jochumsen, Allerød (DK); Morten Sørensen, Ballerup (DK); Thomas Bachgaard Jensen, Vaerløse (DK); Morten Jacobsen, Hørsholm (DK)

(73) Assignee: AMBU A/S, Ballerup (DK)

( * ) Notice: Subject to any disclaimer, the term of this patent is extended or adjusted under 35 U.S.C. 154(b) by 0 days.

(21) Appl. No.: 17/463,028

(22) Filed: Aug. 31, 2021

(65) Prior Publication Data

US 2022/0061645 A1    Mar. 3, 2022

(30) Foreign Application Priority Data

Sep. 2, 2020  (EP) .................................. 20194137

(51) Int. Cl.
*A61B 1/07* (2006.01)
*A61B 1/00* (2006.01)
(Continued)

(52) U.S. Cl.
CPC ............ *A61B 1/07* (2013.01); *A61B 1/00045* (2013.01); *A61B 1/00114* (2013.01);
(Continued)

(58) Field of Classification Search
CPC ....... A61B 1/0008; A61B 1/0676; A61B 1/05; A61B 1/07; A61B 1/00045;
(Continued)

(56) References Cited

U.S. PATENT DOCUMENTS 4,706,653 A    11/1987    Yamamoto
4,753,224 A    6/1988    Tojo
(Continued)

FOREIGN PATENT DOCUMENTS

CN    107174188 A    9/2017
DE    29812048 U1    11/1998
(Continued)

OTHER PUBLICATIONS

European Search Report and Search Opinion Received for EP Application No. 20194137.4, mailed on Feb. 15, 2021, 11 pages.
(Continued)

*Primary Examiner* — Aaron B Fairchild
*Assistant Examiner* — Christen A. Sharpless
(74) *Attorney, Agent, or Firm* — Faegre Drinker Biddle & Reath LLP

(57) ABSTRACT

An endoscope tip part for an endoscope for visually inspecting inaccessible places, including a tip housing enclosing a sealed interior space and including a transparent portion; an image sensor viewing in an optical direction through the transparent portion of the tip housing; a light guide component having a light entry surface and a light exit surface; a first light source having a light-emitting surface and being configured to emit light from the light-emitting surface in a central illumination direction; and an electrical circuit in electrical communication with the image sensor and the first light source, wherein the first light source, the image sensor, and the electrical circuit are accommodated in the sealed interior space of the tip housing, wherein the first light source is attached to the light guide component.

22 Claims, 11 Drawing Sheets

(51) Int. Cl.
*A61B 1/005* (2006.01)
*A61B 1/05* (2006.01)
*F21V 8/00* (2006.01)

(52) U.S. Cl.
CPC .......... *A61B 1/0052* (2013.01); *A61B 1/0057* (2013.01); *A61B 1/051* (2013.01); *G02B 6/0006* (2013.01)

(58) Field of Classification Search
CPC . A61B 1/00114; A61B 1/0052; A61B 1/0057; A61B 1/051; A61B 1/0011; G02B 6/0006
USPC ....................................................... 600/109
See application file for complete search history.

(56) References Cited

U.S. PATENT DOCUMENTS

| | | |
|---|---|---|
| 4,799,130 A | 1/1989 | Emerson |
| 4,805,596 A | 2/1989 | Hatori |
| 4,856,495 A | 8/1989 | Tohjoh et al. |
| 4,860,732 A | 8/1989 | Hasegawa et al. |
| 5,089,895 A | 2/1992 | Fraker et al. |
| 5,193,525 A | 3/1993 | Silverstein et al. |
| 5,193,526 A | 3/1993 | Daikuzono |
| 5,305,736 A | 4/1994 | Ito |
| 5,325,845 A | 7/1994 | Adair |
| 5,379,756 A | 1/1995 | Pileski et al. |
| 5,418,566 A | 5/1995 | Kameishi |
| 5,419,311 A | 5/1995 | Yabe et al. |
| 5,499,625 A | 3/1996 | Frass et al. |
| 5,536,236 A | 7/1996 | Yabe et al. |
| 5,562,602 A | 10/1996 | Yabe et al. |
| 5,575,756 A | 11/1996 | Karasawa et al. |
| 5,609,561 A | 3/1997 | Uehara et al. |
| 5,685,823 A | 11/1997 | Ito et al. |
| 5,688,221 A | 11/1997 | Yabe et al. |
| 5,718,663 A | 2/1998 | Wulfsberg |
| 5,725,476 A | 3/1998 | Yasui et al. |
| 5,788,628 A | 8/1998 | Matsuno |
| 5,836,869 A | 11/1998 | Kudo et al. |
| 5,873,877 A | 2/1999 | Mcgaffigan et al. |
| 5,928,136 A | 7/1999 | Barry |
| 5,993,378 A | 11/1999 | Lemelson |
| 6,181,369 B1 | 1/2001 | Ooshima et al. |
| 6,248,060 B1 | 6/2001 | Buess et al. |
| 6,409,657 B1 | 6/2002 | Kawano |
| 6,503,196 B1 | 1/2003 | Kehr et al. |
| 6,533,722 B2 | 3/2003 | Nakashima |
| 7,442,167 B2 | 10/2008 | Dunki-Jacobs et al. |
| 7,662,093 B2 | 2/2010 | Gilad et al. |
| 7,662,094 B2 | 2/2010 | Iddan |
| 7,798,692 B2 | 9/2010 | Krupa et al. |
| 8,189,062 B2 | 5/2012 | Irion et al. |
| 8,414,480 B2 | 4/2013 | Kendale et al. |
| 8,485,966 B2 | 7/2013 | Robertson |
| 8,790,250 B2 | 7/2014 | Petersen et al. |
| 8,870,753 B2 | 10/2014 | Boulais et al. |
| 8,928,746 B1 | 1/2015 | Stevrin et al. |
| 8,948,560 B1 | 2/2015 | Wach |
| 9,125,582 B2 | 9/2015 | Petersen |
| 9,158,037 B2 | 10/2015 | Otsuka |
| 9,220,400 B2 | 12/2015 | Petersen |
| 9,320,419 B2 | 4/2016 | Kirma et al. |
| 9,521,942 B2 | 12/2016 | Robertson |
| 9,615,730 B2 | 4/2017 | Pascal et al. |
| 9,622,649 B2 | 4/2017 | Lin |
| 9,633,649 B2 | 4/2017 | Bangalore et al. |
| 9,661,998 B2 | 5/2017 | Yoshino |
| 9,814,374 B2 | 11/2017 | Kirma et al. |
| 9,854,962 B2 | 1/2018 | Mcgrail et al. |
| 10,245,402 B2 | 4/2019 | Daher et al. |
| 10,321,804 B2 | 6/2019 | Jacobsen et al. |
| 10,406,309 B2 | 9/2019 | Daher |
| 10,835,103 B2 | 11/2020 | Tamura et al. |
| 2002/0193663 A1 | 12/2002 | Matsuura |
| 2003/0227547 A1 | 12/2003 | Iddan |
| 2004/0027459 A1 | 2/2004 | Segawa et al. |
| 2004/0064018 A1 | 4/2004 | Dunki-Jacobs et al. |
| 2004/0199052 A1 | 10/2004 | Banik et al. |
| 2004/0242963 A1 | 12/2004 | Matsumoto et al. |
| 2005/0203341 A1 | 9/2005 | Welker et al. |
| 2007/0249907 A1* | 10/2007 | Boulais .................. A61B 5/064 600/179 |
| 2008/0055403 A1 | 3/2008 | Salman et al. |
| 2008/0132760 A1 | 6/2008 | Takeuchi |
| 2008/0188715 A1 | 8/2008 | Fujimoto |
| 2008/0200764 A1 | 8/2008 | Okada |
| 2008/0228035 A1* | 9/2008 | Hagihara ............... A61B 1/127 600/176 |
| 2008/0242935 A1 | 10/2008 | Inoue |
| 2008/0266441 A1 | 10/2008 | Ichimura |
| 2009/0012358 A1 | 1/2009 | Ichihashi et al. |
| 2009/0054728 A1 | 2/2009 | Trusty |
| 2009/0177040 A1 | 7/2009 | Yons et al. |
| 2009/0209819 A1 | 8/2009 | Kitagawa et al. |
| 2009/0227998 A1 | 9/2009 | Aljuri |
| 2009/0253964 A1 | 10/2009 | Miyamoto |
| 2009/0292168 A1 | 11/2009 | Farr |
| 2010/0217082 A1 | 8/2010 | Ito et al. |
| 2011/0118549 A1 | 5/2011 | Han |
| 2011/0245617 A1 | 10/2011 | Kitano |
| 2011/0288372 A1 | 11/2011 | Petersen |
| 2011/0295072 A1 | 12/2011 | Boulais et al. |
| 2012/0041268 A1 | 2/2012 | Grey et al. |
| 2012/0041534 A1 | 2/2012 | Clerc |
| 2012/0172664 A1 | 7/2012 | Hayman |
| 2012/0259173 A1 | 10/2012 | Waldron et al. |
| 2012/0323078 A1 | 12/2012 | Kikumori et al. |
| 2013/0035546 A1 | 2/2013 | Lin |
| 2013/0175720 A1 | 7/2013 | Otsuka et al. |
| 2013/0271588 A1 | 10/2013 | Kirma et al. |
| 2014/0073853 A1 | 3/2014 | Swisher et al. |
| 2014/0081085 A1 | 3/2014 | Takato et al. |
| 2014/0150782 A1 | 6/2014 | Vazales et al. |
| 2014/0313766 A1 | 10/2014 | Krupa et al. |
| 2014/0328047 A1 | 11/2014 | Kamee et al. |
| 2015/0005580 A1 | 1/2015 | Petersen |
| 2015/0036146 A1 | 2/2015 | Staloff |
| 2015/0335227 A1 | 11/2015 | Jacobsen et al. |
| 2016/0029879 A1 | 2/2016 | Ishikawa |
| 2016/0051222 A1 | 2/2016 | Imahashi |
| 2016/0106306 A1 | 4/2016 | Furuta |
| 2016/0278620 A1 | 9/2016 | Kawayoke |
| 2016/0287060 A1 | 10/2016 | Usuda |
| 2017/0108691 A1 | 4/2017 | Kitano |
| 2017/0108692 A1 | 4/2017 | Kitano |
| 2017/0245734 A1 | 8/2017 | Kaneko |
| 2017/0251914 A1 | 9/2017 | Kitano |
| 2017/0307872 A1 | 10/2017 | Hatase et al. |
| 2017/0325663 A1 | 11/2017 | Levy et al. |
| 2018/0070803 A1 | 3/2018 | Mikami |
| 2018/0078120 A1 | 3/2018 | Poll et al. |
| 2018/0084981 A1 | 3/2018 | Wang |
| 2018/0132700 A1 | 5/2018 | Ouyang et al. |
| 2018/0160886 A1 | 6/2018 | Govani et al. |
| 2018/0310890 A1 | 11/2018 | Li |
| 2018/0317756 A1 | 11/2018 | Unsai |
| 2019/0033506 A1 | 1/2019 | Weber et al. |
| 2019/0089875 A1 | 3/2019 | Fan |
| 2019/0175007 A1* | 6/2019 | Sørensen ............ A61B 1/00117 |
| 2019/0183325 A1 | 6/2019 | Troller et al. |
| 2019/0227298 A1 | 7/2019 | Elmaanaoui |
| 2019/0246027 A1 | 8/2019 | Kuhn et al. |
| 2019/0282070 A1 | 9/2019 | Vilhelmsen et al. |
| 2019/0282077 A1 | 9/2019 | Sørensen et al. |
| 2019/0298161 A1 | 10/2019 | Jensen |
| 2019/0313891 A1 | 10/2019 | Oka |
| 2019/0350442 A1 | 11/2019 | Giessen et al. |
| 2019/0374092 A1 | 12/2019 | Wu et al. |
| 2020/0100662 A1 | 4/2020 | Jensen et al. |
| 2020/0110256 A1 | 4/2020 | Altshuler et al. |
| 2020/0196434 A1 | 6/2020 | Kuo et al. |
| 2020/0214543 A1 | 7/2020 | Ben-Arye |
| 2020/0288953 A1 | 9/2020 | Srensen et al. |

(56) References Cited

U.S. PATENT DOCUMENTS

| | | |
|---|---|---|
| 2020/0305699 A1 | 10/2020 | Herriges et al. |
| 2021/0022588 A1 | 1/2021 | Schultheis et al. |
| 2021/0127955 A1 | 5/2021 | Srensen et al. |
| 2021/0282631 A1* | 9/2021 | Schultheis ........... A61B 1/0669 |
| 2021/0338062 A1 | 11/2021 | Do |
| 2022/0175226 A1 | 6/2022 | Sorensen et al. |

FOREIGN PATENT DOCUMENTS

| | | |
|---|---|---|
| DE | 102017107755 A1 | 10/2018 |
| DE | 102018102587 B3 | 1/2019 |
| DE | 102018107523 A1 | 10/2019 |
| DE | 102018126794 A1 | 4/2020 |
| EP | 0677272 A1 | 10/1995 |
| EP | 0756845 A1 | 2/1997 |
| EP | 0941691 A1 | 9/1999 |
| EP | 1494574 B1 | 2/2012 |
| EP | 1971888 B1 | 8/2017 |
| EP | 3 539 449 | 9/2019 |
| EP | 3539446 A1 | 9/2019 |
| EP | 3539447 A1 | 9/2019 |
| JP | 03-264037 A | 11/1991 |
| JP | 2004-016455 A | 1/2004 |
| JP | 2004-029235 A | 1/2004 |
| JP | 2005-304812 A | 11/2005 |
| JP | 3764512 B2 | 4/2006 |
| JP | 2009-125528 A | 6/2009 |
| JP | 2010-169802 A | 8/2010 |
| JP | 4914638 B2 | 4/2012 |
| JP | 2013-009896 A | 1/2013 |
| JP | 5503965 B2 | 5/2014 |
| JP | 2018-015250 A | 2/2018 |
| WO | 2005/023099 A1 | 3/2005 |
| WO | 2008/115575 A1 | 9/2008 |
| WO | 2010/066789 A1 | 6/2010 |
| WO | 2010/066790 A1 | 6/2010 |
| WO | 2010/129324 A2 | 11/2010 |
| WO | 2012/077116 A1 | 6/2012 |
| WO | 2012/077117 A1 | 6/2012 |
| WO | 2014/106511 A1 | 7/2014 |
| WO | 2014/188787 A1 | 11/2014 |
| WO | 2015/056106 A2 | 4/2015 |
| WO | 2016/188537 A1 | 12/2016 |
| WO | 2016/188541 A1 | 12/2016 |
| WO | 2017/104048 A1 | 6/2017 |
| WO | 2018/042715 A1 | 3/2018 |
| WO | 2018/059643 A1 | 4/2018 |
| WO | 2019/049159 A1 | 3/2019 |
| WO | 2019/087178 A1 | 5/2019 |

OTHER PUBLICATIONS

Extended Search Report in related European Application No. 20212500.1, dated Mar. 9, 2021, 7 pgs.

* cited by examiner

ENDOSCOPE TIP PART

CROSS-REFERENCE TO RELATED APPLICATIONS

This application claims the benefit of and priority from European Patent Application No. 20194137.4, filed on Sep. 2, 2020, which is incorporated herein by reference in its entirety.

TECHNICAL FIELD

The present disclosure relates to an endoscope tip part, a light guide component for an endoscope tip part, an endoscope, and a method of assembling an endoscope tip part.

BACKGROUND

Insertion endoscopes are well-known devices in the medical field for visually examining the interior of a hollow organ or cavity of a body, such as lungs, by means of inserting an insertion portion of the endoscope. The insertion portion of the endoscope comprises an elongated insertion tube, a tip part, and a bending section connecting the insertion tube with the tip part. The endoscope typically has a handle connected to the insertion tube and positioned at the proximal end of the endoscope as seen from the operator. The endoscope further has an imaging subassembly with an image sensor built in the tip part at the distal end of the endoscope.

This definition of proximal as being closest to an operator and distal as being furthest from an operator is used throughout this disclosure. Illumination of the area in front of the distal tip of the endoscope is normally required, in particular the field of vision of the image sensor. One known way of achieving such illumination is to incorporate one or more light sources, such as Light-emitting Diodes (LEDs), and one or more light guides in the tip part of the endoscope, e.g. as mentioned in EP 19 161 893 disclosing a disposable endoscope.

The present disclosure makes a distinction between optical fibres and light guides. Optical fibres in this context are to be understood as highly elongated and flexible elements, where the length is several orders of magnitude larger than the diameter, providing the fibres with a high degree for flexibility to allow them to conduct luminous flux to a desired place. Light guides are to be understood as much shorter, preferably rigid elements adapted to guide and distribute light in a desired manner. Furthermore, while optical fibres are used to transport light, as used herein light guides are primarily used to reshape the incoming light beam.

The bending section is provided in order to manoeuvre the endoscope inside the body cavity. The bending section has increased flexibility, e.g. achieved by a number of articulated segments of which the tip part forms the distalmost segment. Bending or straightening of the bending section in the insertion part of the endoscope is typically done by tensioning or slacking, respectively, steering wires running from the tip part through the remainder of articulated segments and along the inside of the elongated insertion tube to a control mechanism, such as a control lever, of the handle.

Data and/or power cables for the image sensor and other electronics, such as LED lighting accommodated in the tip part at the distal end of the endoscope, run along the inside of the elongated insertion tube and the bending section from the handle to the tip part. Furthermore, a working channel may run along the inside of the insertion tube and the bending section from the handle to the tip part, e.g. allowing liquid to be removed from the body cavity or allowing the insertion of medical tools or surgical instruments into the body cavity.

One of the parameters driving the number of medical applications for which the endoscope can be used, is the outer diameter of the insertion tube and the endoscope tip part. Thus, an ongoing goal in the field is to minimise this outer diameter to enable the endoscope to inspect smaller bodily ducts, e.g. further into the branches of the bronchial tree or nasal passages. However, in such a miniaturised tip part it is difficult to ensure consistent optical performance of the image sensor and light source.

SUMMARY

In light of the above, it may be seen as an object of the present disclosure to provide a miniaturised endoscope tip part while reducing the variance in the optical properties of the imaging means and light source.

Another object of the present disclosure is to provide a method of assembling a tip part which reduces the variance in the optical properties of the imaging means and light source.

One or more of these objects may be met by aspects of the present disclosure as described in the following.

A first aspect of this disclosure relates to an endoscope tip part for an endoscope for visually inspecting inaccessible places, such as human body cavities, the endoscope tip part having an exterior surface and extending along a longitudinal axis and comprising:
- a tip housing extending along the longitudinal axis and at least partially enclosing a sealed interior space, the tip housing including:
  - an exterior housing surface for forming a first part of the exterior surface of the endoscope tip part, and
  - a transparent portion, such as a window or a front lens, having an interior surface facing the sealed interior space of the endoscope tip part and an exterior surface forming a second part of the exterior surface of the endoscope tip part;
- an imaging subassembly including an image sensor viewing in an optical direction through the transparent portion of the tip housing;
- a light guide component comprising a first light guide having a light entry surface and a light exit surface, the first light guide being configured for propagating light received through the light entry surface out through the light exit surface and the transparent portion of the tip housing;
- a first light source preferably having a light-emitting surface and being configured to emit light, preferably from the light-emitting surface, in a central illumination direction to be received by the light entry surface of the first light guide, preferably the central illumination direction being at least partially oriented in the optical direction of the image sensor; and
- an electrical circuit comprising a first circuit portion in electrical communication with the image sensor and preferably a second circuit portion in electrical communication with the first light source, the electrical circuit being configured for transmitting an image signal generated by the image sensor indicative of the view in the optical direction, preferably to a handle of the endoscope;

wherein the first light source, the image sensor, and the electrical circuit are accommodated in the sealed interior space of the tip housing, wherein the first light source is attached, preferably directly attached, to the light guide component and preferably positioned proximally relative to the image sensor.

By attaching the light source, preferably directly, to the light guide component, the loss of and variation in power of light due to varying offset position of the light source in relation to the light guide component. Furthermore, the variance in a gap distance between the light source and the light guide component can be reduced or even avoided by directly attaching the light source to the light guide component. This has the advantage of reducing power losses and power variances. A further advantage of such an arrangement is reducing the risk of adhesive sealing the interior space enters between the light source and the light guide component during application as this can cause reduced optical performance, such as reduced illumination power or illumination colour shifting. An additional advantage is that such an arrangement is easier to assemble, especially when the tip part is miniaturised as the light source and the light guide component is an integrated assembly.

In the present disclosure, a direct attachment between two parts may be defined as the two parts are attached via attachment means without an intermediate connector part. An example of a direct attachment are two parts adhered together so that the same adhesive contacts both elements. An example of an indirect attachment is the attachment between the tip part and the handle which is provided via the bending section and the insertion tube.

Additionally or alternatively, the light guide(s) may be configured to transmit light received by the respective light entry surface, past the imaging subassembly, and out through the respective light exit surface.

Additionally or alternatively, the first and/or second light guide(s) consist(s) essentially of a polymer material and the circumferential surface of the first and/or second light guide defines a polymer-air interface.

Additionally or alternatively, the endoscope may comprise one or more optical redirection component(s) arranged between the corresponding light source and the corresponding light guide. The optical component(s) may be configured for reflecting or mirroring light emitted from the light source(s) towards the light entry surface of the corresponding light guide.

Additionally or alternatively, the tip housing may extend along a longitudinal axis and may comprise a wall extending circumferentially around the longitudinal axis. The wall may have a cylinder shell shape. The transparent portion may close off a distal end of the wall.

Additionally or alternatively, the tip housing may be formed as a monolithic piece. The transparent portion of the tip housing is preferably formed of a transparent material.

Additionally or alternatively, the tip housing may be manufactured by a single-shot injection moulding, preferably of a transparent material. This is a simple and cheap way of manufacturing the tip housing. Alternatively, the tip housing may be manufactured by a multi-shot injection moulding process comprising at least two shots. The wall may be formed by a shot, preferably of an opaque material, and the transparent portion may be formed by another shot, preferably of a transparent material. By forming part of the tip housing in a different material allows tailoring that part to have specific properties, for instance that part may be formed of an opaque material which may prevent stray light from entering the image sensor.

Additionally or alternatively, the transparent portion is preferably a window. The transparent portion may be formed in a distal end face of the tip housing.

Additionally or alternatively, the endoscope tip part may comprise a plug sealing a proximal opening of the wall, e.g. by an adhesive. The plug may be formed separately from housing.

Additionally or alternatively, the sealed interior space is filled with air. In particular, the light guide(s) or the circumferential surface of the light guide(s) being surrounded by air. The interior space may be accessible by the proximal opening, and the tip housing may enclose the interior space so that the proximal opening is the only access to the interior space.

Additionally or alternatively, the light source(s) may comprise a light-emitting diode configured for emitting substantially white light. The light-emitting diode may be a single light-emitting diode, which is also known as a single-die light-emitting diode. Additionally, the light-emitting diode may be phosphor-based which is particularly suited, as it can emit white light and is compact.

In any case, the light-emitting diode may comprise a semiconductor die surrounded by a cover which is typically epoxy-based. Alternatively, the light source(s) may comprise a plurality of light-emitting diodes, such as three, each configured for emitting a light of a different wavelength, such as red, green, and blue light. The plurality of light-emitting diodes may be covered by a cover and may be arranged so that the light emitted from the cover is substantially white. In both cases, an exterior surface of the cover may define the light-emitting surface of the light source(s). Alternatively, the light source(s) may comprise one or more optical fibres configured for transmitting light from an external light source, such as a light-emitting diode, positioned outside of the endoscope tip part, such as positioned in the handle. The light-emitting surface(s) may thus form part of the one or more optical fibres.

Additionally or alternatively, the central illumination direction of the light source(s) may be at least partially oriented in, preferably parallel to, the optical direction of the image sensor. This may have the advantage of reducing light losses, as the redirection of the emitted light beam of the light source is reduced. The central illumination direction of the light source(s) may intersect the light entry surface of the corresponding light guide.

Alternatively, the central illumination direction of the light source(s) may be substantially perpendicular to the optical direction of the image sensor. This has the advantage of allowing for a more compact arrangement of the light source(s).

Additionally or alternatively, the imaging subassembly may comprise a lens arrangement including one or more lenses aligned with the optical direction and between the interior surface of the transparent portion and the image sensor so that the image sensor views through the lens arrangement and the transparent portion.

Additionally or alternatively, the first light source may be an electrical component, such as one or more light-emitting diodes, and the electrical circuit may comprise a second circuit portion in electrical communication with the first light source.

Additionally or alternatively, the electrical circuit may be provided on a printed circuit board (PCB). The electrical circuit may comprise a main circuit portion for interconnecting various electronic components, e.g. capacitors, transistors, and the like, of the printed circuit board. The first circuit portion of the electrical circuit may electrically connect the image sensor to the main circuit portion and the second circuit portion of the electrical circuit may electrically connect the light source(s) with the main circuit portion.

The first circuit portion and/or the second circuit portion may be flexible so that, prior to assembly, the image sensor and light source(s) are movable relative to each other. In this case, the electrical circuit may be provided on a flexible circuit board (FPC). This may be an advantage in assembly, as the image sensor and light source(s) can be moved relatively to their desired position irrespective of production tolerances.

The electrical circuit may be configured for transmitting the image signal to an electrical component, such as a circuit board, positioned in the handle. The image signal may be transmitted from the electrical circuit of the endoscope tip part via a wired connection or a wireless connection. Thus, the electrical circuit does not necessarily comprise a cable extending between the tip part and the handle for transmitting the image signal.

Additionally or alternatively, the endoscope tip part may comprise a frame part for supporting the electrical circuit. In particular, the electrical circuit may be provided on a folded FPC being folded around the frame part.

Additionally or alternatively, the light guide component may comprise a second light guide having a light entry surface and a light exit surface, the second light guide being configured for propagating light received through the light entry surface out through the light exit surface and the transparent portion of the tip housing. Additionally, the endoscope tip part may comprise a second light source having a light-emitting surface and being configured to emit light from the light-emitting surface in a central illumination direction to the light entry surface of the second light guide, preferably the central illumination direction of the second light source being at least partially oriented in the optical direction of the image sensor. Additionally or alternatively, a surface normal of the light-emitting surface of the second light source may be at least partially oriented in the optical direction of the image sensor.

The second light source may be attached, preferably directly attached, to the light guide component and preferably positioned proximally relative to the image sensor, and wherein the first and second light guides extend side-by-side or in parallel on opposite sides of the imaging subassembly, preferably the image sensor.

By having a light guide component with both a first and a second light guide, assembly of the tip part is further improved as the light guides can be handled as a single component. Further advantages of attaching the first light source to the light guide component as previously described is achieved also for the second light source.

Additionally or alternatively, the light guide exit(s) may comprise a collar at least partially surrounding the respective light guide, and the interior surface of the transparent portion may comprise a seat or seats for receiving the respective collar. Each seat may be formed as a rail or a depression for retaining the respective light guide. This may be advantageous for assembling the endoscope tip part.

Additionally or alternatively, the light guide component may be formed separately from the tip housing, and wherein the first light guide exit and optionally the second light guide exit are oriented towards the interior surface of the transparent portion.

Such an arrangement is particularly advantageous for assembly, as the light source(s) can be attached to the light guide component outside of the tip housing and then subsequently assembled with the tip housing.

The second light guide may be identical or be symmetric to the first light guide, and the second light source may be identical or be symmetric to the first light source. This may improve the light distribution in the field of view of image sensor.

Additionally or alternatively, the tip housing may comprise a distal end face and a proximal opening providing access to the sealed interior space, wherein the distal end face is preferably positioned opposite of the proximal opening, and wherein the distal end face comprises at least part of the exterior surface of the transparent portion, preferably the entirety of the exterior surface of the transparent portion.

Additionally or alternatively, the first and/or the second light source(s) may be at least partially overlapping the imaging subassembly, preferably the image sensor, when viewed in a cross-section perpendicular to the longitudinal axis.

This has the advantage of allowing a more compact arrangement of the light source(s) and imaging subassembly, as the light source(s) can be packed behind the image sensor and thus reduce(s) the combined diameter of the light source(s), and the imaging subassembly thereby allowing a smaller outer diameter of the tip housing.

Additionally or alternatively, the first and/or the second circuit portion(s) may be flexible circuit structures, preferably so that, prior to assembly, the image sensor and light source(s) are movable relative to each other via flexing of first and/or second circuit portions.

Since optimum optical performance is achieved by positioning the imaging subassembly and light source(s) with a predetermined relative distance, the flexible circuit portion(s) has/have the advantage of allowing the assembler to move the parts relative to each other and thus absorb this variance.

Additionally or alternatively, the first and/or the second light guide(s) may consist essentially of a transparent material with a first refractive index, and wherein the light-emitting surface of the light source(s) may be adhered to the light entry surface of the respective light guide by an adhesive preferably with a second refractive index within +/−0.2, preferably within +/−0.1, of the first refractive index.

By adhering the light source(s) to the light entry surface of the respective light guide, the gap between these two elements is eliminated, thus increasing the illumination power of the light source(s). By configuring the first and second refractive indices to be similar, the less desirable optical effects of having an adhesive layer between the light guide and light source is reduced or even eliminated.

A second aspect of this disclosure relates to a light guide component for an endoscope tip part, such as an endoscope tip part according to the first aspect, the light guide component comprising:
  a first and a second light guide being spaced apart by a gap and extending, preferably side-by-side or in parallel, along a respective longitudinal center line, wherein each light guide has a proximal end, a distal end, a light entry surface at the proximal end, a light exit surface at the distal end, and a circumferential surface extending from the light entry surface to the light exit surface around the respective longitudinal center line, and
  a crossmember extending transversely from the first light guide to the second light guide, preferably over the gap so as to form a unitary rigid light guide component, wherein the light guides are configured for propagating light received through the respective light entry surface out through the respective light exit surface, preferably while minimising light loss through the respective circumferential surface.

Such a light guide component has the advantage of easing assembly of two spaced-apart light guides in a miniaturised tip housing since they can be handled as a unitary component by means of the crossmember.

Additionally or alternatively, the light guides may be reflection-symmetric in a first plane extending at a distance between the light guides, i.e. does not intersect the light guides.

Additionally or alternatively, the first and/or the second light guide(s) may be reflection-symmetric in a second plane comprising the longitudinal center line and preferably intersecting the first plane.

Additionally or alternatively, the first and/or the second light guide(s) may be reflection-asymmetric in a third plane being perpendicular to the second plane and comprising the longitudinal center line and preferably intersecting the first plane.

Additionally or alternatively, the longitudinal center line of each light guide may be straight or curved. The longitudinal center lines may be extending side-by-side or preferably in parallel.

Additionally or alternatively, each light guide may be a single moulded component.

Additionally or alternatively, each light guide may have a varying cross-section along the respective longitudinal center line. Each light guide may comprise a transition portion including the respective light entry surface having a varying cross section along the longitudinal center line. Each light guide may further comprise a straight portion extending directly from the transition portion, the straight portion having a substantially constant cross-section along the longitudinal center line. The transition portion may taper with a taper angle with respect to the longitudinal axis, wherein the taper angle is in the range of 1-12 degrees, preferably in the range of 5-10 degrees, or more preferably in the range of 7-10 degrees.

Additionally or alternatively, the light guide(s), in particular the straight portion of each light guide, may have a width and a height. The width may be in the range of 0.35-0.55 mm or preferably in the range of 0.4-0.5 mm. The height may be in the range of 0.6-0.8 mm or preferably in the range of 0.65-0.75 mm.

Additionally or alternatively, the gap spacing apart the light guides may have a distance transversely to the longitudinal axis in the range of 1.3-1.8 mm, preferably in the range of 1.4-1.7 mm.

Additionally or alternatively, the first and/or second light guide(s) may be made of a material with a refractive index that is higher than the refractive index of air. This ensures that the critical angle for total internal reflection of light incident on the circumferential surface of the respective light guide is also increased, thus increasing the ability of the respective light guide to transmit light from entry to exit.

Additionally or alternatively, the first light guide component comprises a rail or rails at least partially surrounding one or both light entry surfaces, the rail(s) being configured to retain a light source attached to the respective light guide.

Additionally or alternatively, the crossmember may be opaque or may be formed of an opaque material.

In the context of this disclosure, a light guide is not regarded as the same as an optical fibre. An optical fibre is typically long and thin, i.e. the length is several orders of magnitudes larger than the diameter and thus flexible providing the fibres with a high degree of flexibility to allow them to transmit luminous flux to a desired place without reshaping the light beam. Optical fibres are also typically arranged in a bundle. In contrast, a light guide is to be understood as much shorter, i.e. typically the length is typically within the same or one order of magnitude larger than the diameter, and preferably rigid, typically made in a single piece (e.g. monolithically formed) of a transparent material. A light guide also differs in function in that it is adapted to guide and reshape the incoming light beam in a desired manner. Further an optical fibre typically comprises an opaque sheath while a light guide typically is monolithically formed without a sheath.

Additionally or alternatively, the crossmember may extends transversely, preferably over the gap, from the proximal end of the first light guide to the proximal end of the second light guide.

This may be advantageous for facilitating assembly, as the assembler can push on the crossmember to ensure that the light guide component is desirably positioned in the housing. The crossmember may also in this way partition the tip housing in a proximal and distal portion and may thus aid in sealing the light guide component.

Alternatively, the crossmember may extend transversely over the gap from the distal end of the first light guide to the distal end of the second light guide. Alternatively, the crossmember may extend transversely over the gap from a central portion of the first light guide to a central portion of the second light guide, the central portions being located between the proximal and distal portion of the respective light guide.

Additionally or alternatively, the crossmember may partition the interior space in a proximal interior space and a distal interior space closed by the crossmember, the distal interior space accommodating the imaging subassembly.

Additionally or alternatively, the light guide component is formed monolithically, and may preferably be manufactured by a moulding process, such as an injection moulding process.

Additionally or alternatively, the light guide component, i.e. the first light guide, second light guide, and the crossmember, is made of a single transparent polymer material.

Additionally or alternatively, the light guide component may be manufactured by single-shot injection moulding, preferably of a transparent material. This is a simple way of manufacturing the light guide component. Alternatively, the light guide component may be manufactured by a multi-shot injection moulding process comprising at least two shots. The crossmember may be formed by a shot, preferably of an opaque material, and the first and second light guides may be formed by another shot, preferably of a transparent material. By forming part of the crossmember in an opaque material may prevent stray light from entering the image sensor.

Additionally or alternatively, the light entry surfaces of the first and second light guides may be planar and preferably parallel, and/or light exit surfaces of the first and second light guides may be planar and preferably parallel. In a preferably embodiment, all the light entry surfaces and the light exit surfaces are planar and parallel.

Additionally or alternatively, a gap may be located between the crossmember and the tip housing. The gap may be substantially uniform about the longitudinal axis. The gap may be sealed by an adhesive.

A third aspect of this disclosure relates to an endoscope for visually inspecting inaccessible places such as human body cavities, the endoscope comprising:

a handle for gripping by an operator and comprising a control device;
an endoscope tip part according to the first aspect of this disclosure;
an insertion tube for insertion into a patient, the insertion tube extending from the handle to the endoscope tip part and comprising a bending section;
one or more cables running through the insertion tube and electrically connecting the electrical circuit of the endoscope tip part with the handle; and
at least one steering wire connecting the handle with a distal end of the bending section so that manipulation of the control device causes bending of the bending section.

A fourth aspect of this disclosure relates to an endoscope system for visually inspecting inaccessible places, such as human body cavities, the endoscope system comprising a monitor and an endoscope according to the third aspect or an endoscope comprising an endoscope tip part according to the first aspect, wherein the endoscope is connectable to the monitor, and the monitor is configured for displaying an image captured by the image sensor of the endoscope tip part.

A fifth aspect of this disclosure relates to a method for assembling an endoscope tip part, such as an endoscope tip part according to the first aspect, the endoscope tip part extending along a longitudinal axis, the method comprising the steps of:
providing:
  a housing extending along the longitudinal axis and at least partially enclosing an interior space, the tip housing including:
  a proximal opening providing access to the interior space,
  an exterior housing surface for forming an exterior surface of the endoscope tip part, and
  a transparent portion, such as a window or a front lens, having an interior surface and an exterior surface, the interior surface facing the interior space of the endoscope tip part and the exterior surface facing the exterior of the endoscope tip part,
  an imaging subassembly including an image sensor viewing in an optical direction,
  a light guide component comprising a first light guide including a proximal end, a distal end, a light entry surface at the proximal end, a light exit surface at the distal end, and a circumferential surface extending from the light entry surface to the light exit surface around the respective longitudinal center line, the first light guide being configured for propagating light received through the light entry surface out through the light exit surface, preferably while minimising light loss through the circumferential surface,
  a first light source having a light-emitting surface and being configured to emit light from the light-emitting surface in a central illumination direction, and
  an electrical circuit comprising a first circuit portion in electrical communication with the image sensor and a second circuit portion in electrical communication with the light source(s), the electrical circuit being configured for transmitting an image signal generated by image sensor indicative of the view in the optical direction, preferably to a handle of the endoscope, wherein at least one of the first and second circuit portions is flexible so the image sensor and light source(s) are movable relative to each other;
attaching the first light source, preferably directly, to the light guide component, preferably to the first light guide, so that light emitted by the first light source is received by the light entry surface of the first light guide, and so that the imaging subassembly, the light guide component, and the electrical circuit forms a main subassembly;
inserting the main subassembly through the proximal opening of the tip housing into the interior space so that the optical direction of the image sensor extends through the transparent portion, and so that a surface normal of the light exit surface of the first light guide is at least partially oriented towards the interior surface of the transparent portion;
fixing the main subassembly to the tip housing and sealing the proximal opening to seal the interior space.

Additionally or alternatively, the light guide component may be provided according to the second aspect of this disclosure.

Additionally or alternatively, the method may further comprise a step, preferably performed prior to the step of inserting, of:
arranging the main subassembly in a jig, adjusting the light guide component relative to the imaging subassembly to a predetermined relative position along the longitudinal direction via flexing of the first and/or second circuit portion(s), and subsequently fixing, preferably by adhering, the light guide component relative to the imaging subassembly,
wherein the step of inserting the main subassembly comprises inserting the main subassembly along the longitudinal direction until a distal end of the imaging subassembly abuts an interior distal portion of the tip housing, preferably the interior surface of the transparent portion, and until a distal end of the light guide component, preferably the light exit surface of the first light guide, abuts an interior distal portion of the tip housing, preferably the interior surface of the transparent portion.

In the present disclosure, a partial orientation of a surface in a direction may be defined as an angle between a surface normal of said surface and said direction being acute or zero, e.g. that the light-emitting surface is at least partially oriented in the optical direction may be defined as a surface normal of the light-emitting surface and the optical direction form an acute angle or are parallel, and an orientation of a surface towards an element may be defined as a surface normal of said surface intersects said element.

A person skilled in the art will appreciate that any one or more of the above aspects of this disclosure and embodiments thereof may be combined with any one or more of the other aspects of this disclosure and embodiments thereof.

BRIEF DESCRIPTION OF THE DRAWINGS

Embodiments of this disclosure will be described in more detail in the following detailed description with regard to the accompanying figures. The figures show one or more ways of implementing the present invention and are not to be construed as being limiting to other possible embodiments falling within the scope of the attached claim set.

DETAILED DESCRIPTION

Figure 1:
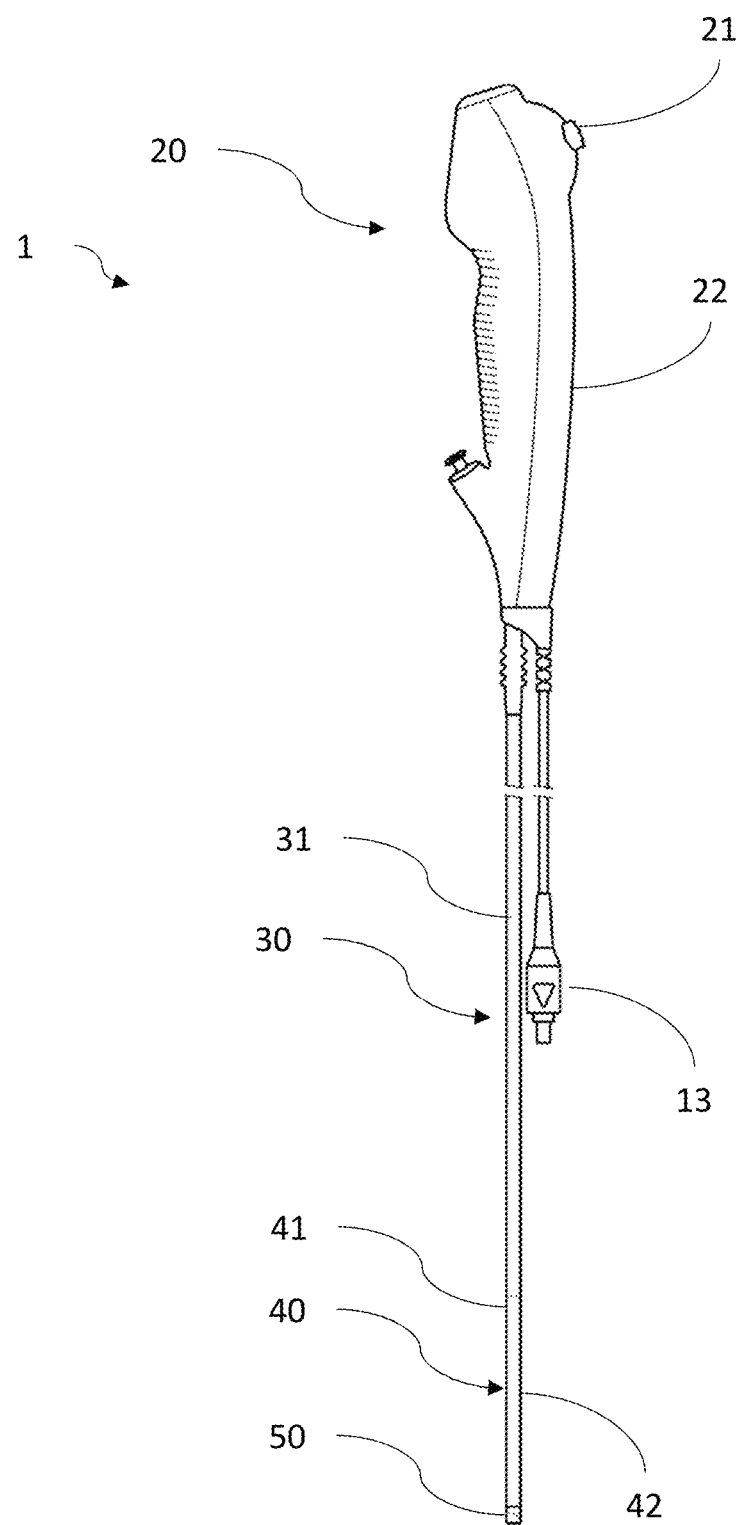
FIG. 1 is a schematic perspective illustration of an endoscope according to this disclosure.
Figure 2:
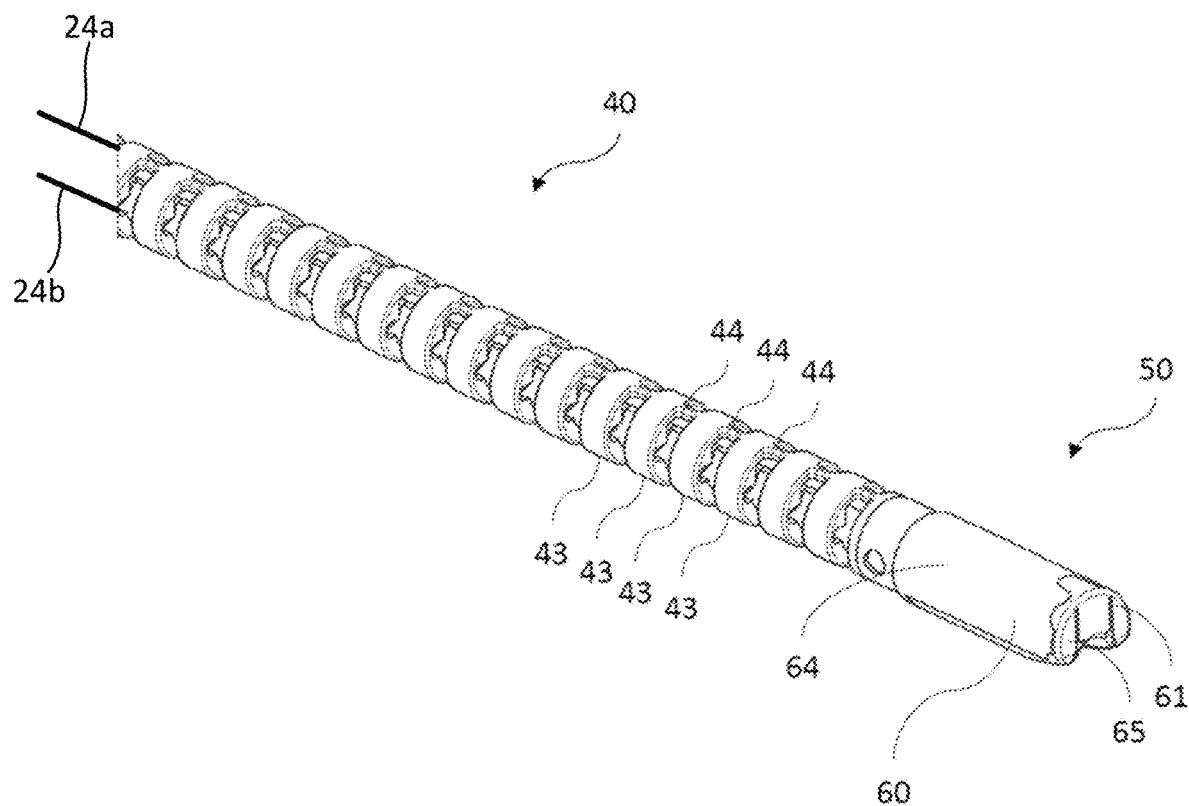
FIG. 2 is a schematic perspective illustration of a distal tip and a bending section of the endoscope shown in FIG. 1.

FIG. 1 illustrates an endoscope 1, which is disposable and not intended to be cleaned and reused. The endoscope 1 comprises an endoscope tip part 50, a handle 20 with a handle housing 22 for gripping and a control lever 21, and an insertion tube 30 for insertion into a patient and extending between the handle 20 and a proximal end 41 of a bending section 40. The insertion tube 30 has an exterior tubular surface 31 providing a barrier against the surroundings of the endoscope 1. The bending section 40 comprises articulated segments 43, hinges 44 connecting the segments 43 as best seen in FIG. 2, and a thin outer sleeve 42. The endoscope 1 further comprises two steering wires (24a, 24b) extending inside the insertion tube 30 from the control lever 21 of the handle 20 to the distal tip part 50 and arranged in a Bowden cable configuration so that an operator can, upon manipulation of the control lever 21, articulate the segments 43 of the bending section about their respective hinges 44 to cause bending of the bending section 40. The thin outer sleeve 42 covers the segments 43, the hinges 44, and the gaps between the segments 43, thereby providing a smooth outer surface for the bending section 40 in order to improve the comfort of a patient undergoing endoscopy, especially when the operator articulates the bending section 40. The thin outer sleeve 42 further provides an additional layer of sealing for the connection between the endoscope tip part 50 and the bending section 40. Furthermore, a working channel (not shown) runs along the inside of the insertion tube from the handle 20 to a working channel opening (not shown) of the endoscope tip part 50, e.g. allowing liquid to be removed from the body cavity or allowing the insertion of medical tools or surgical instruments into the body cavity.

Figure 3:
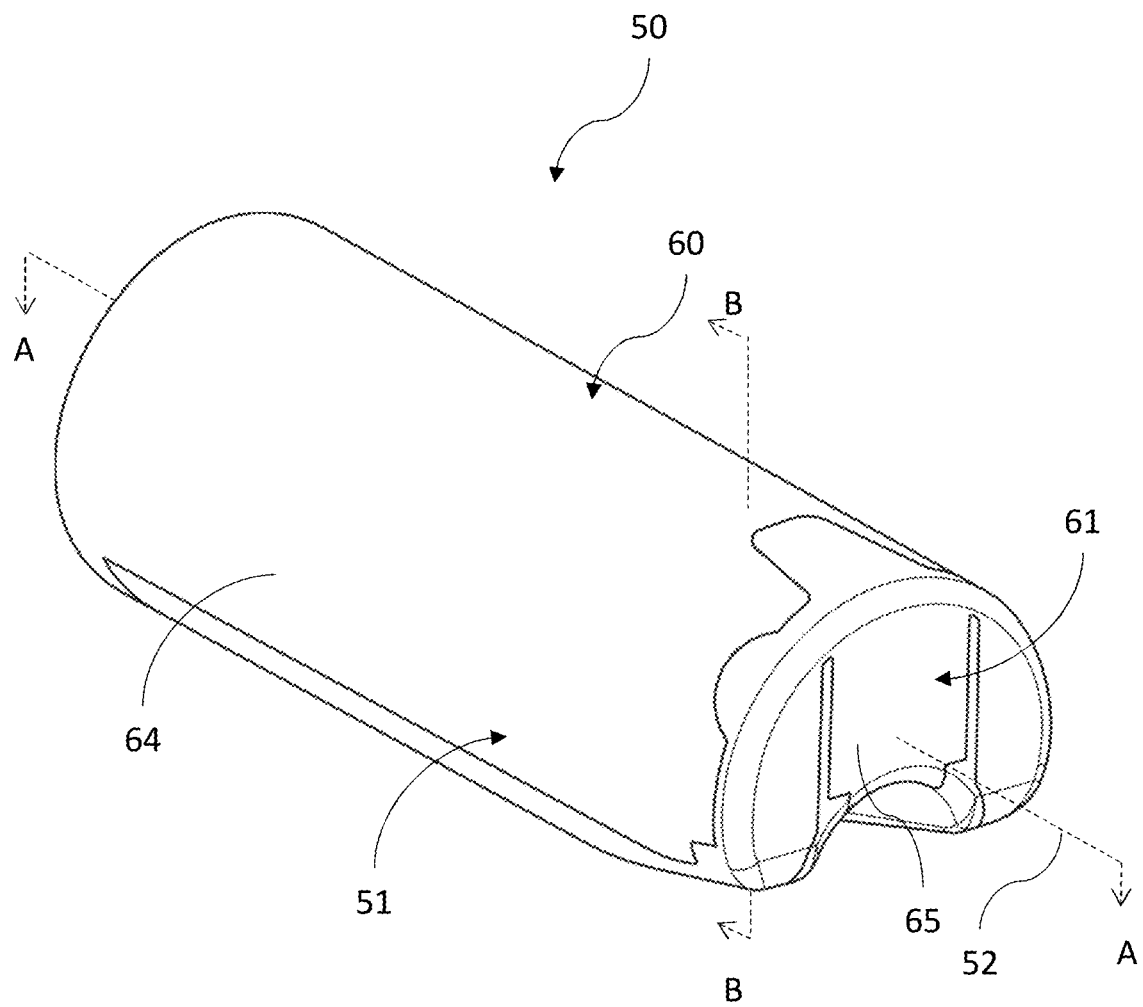
FIG. 3 is a schematic perspective illustration of the distal tip of FIG. 2 without the bending section.
Figure 4A:
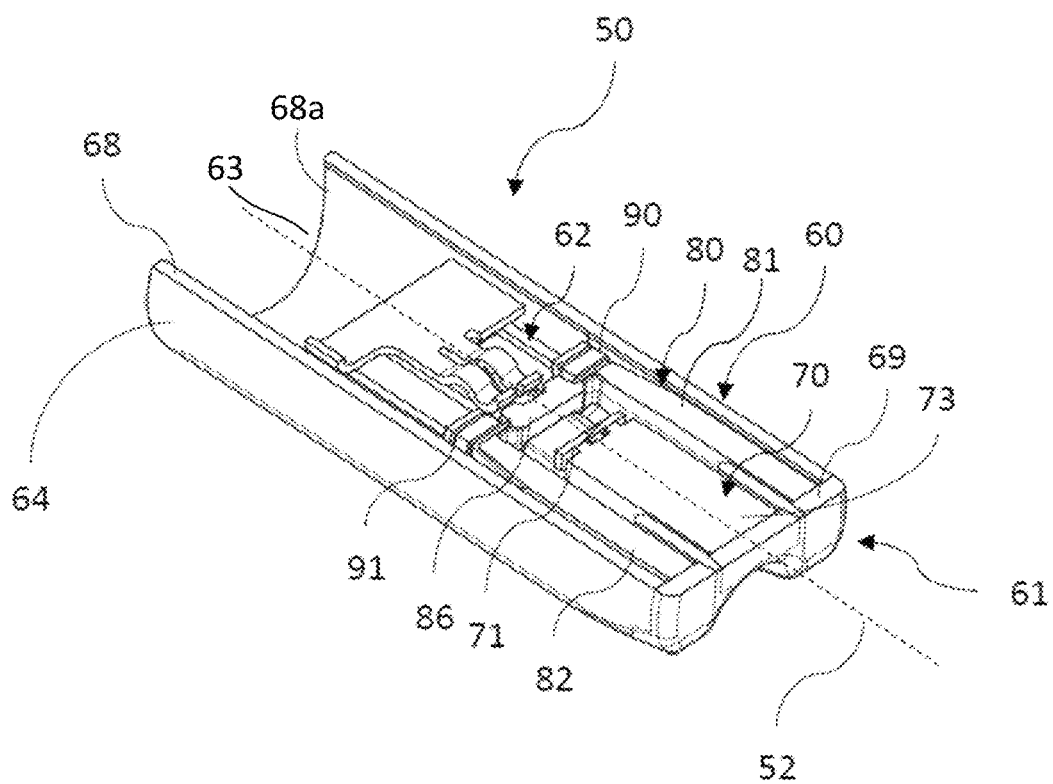
FIG. 4a is a schematic perspective cross-sectional illustration of the distal tip along the A-A line of FIG. 3.
Figure 4B:
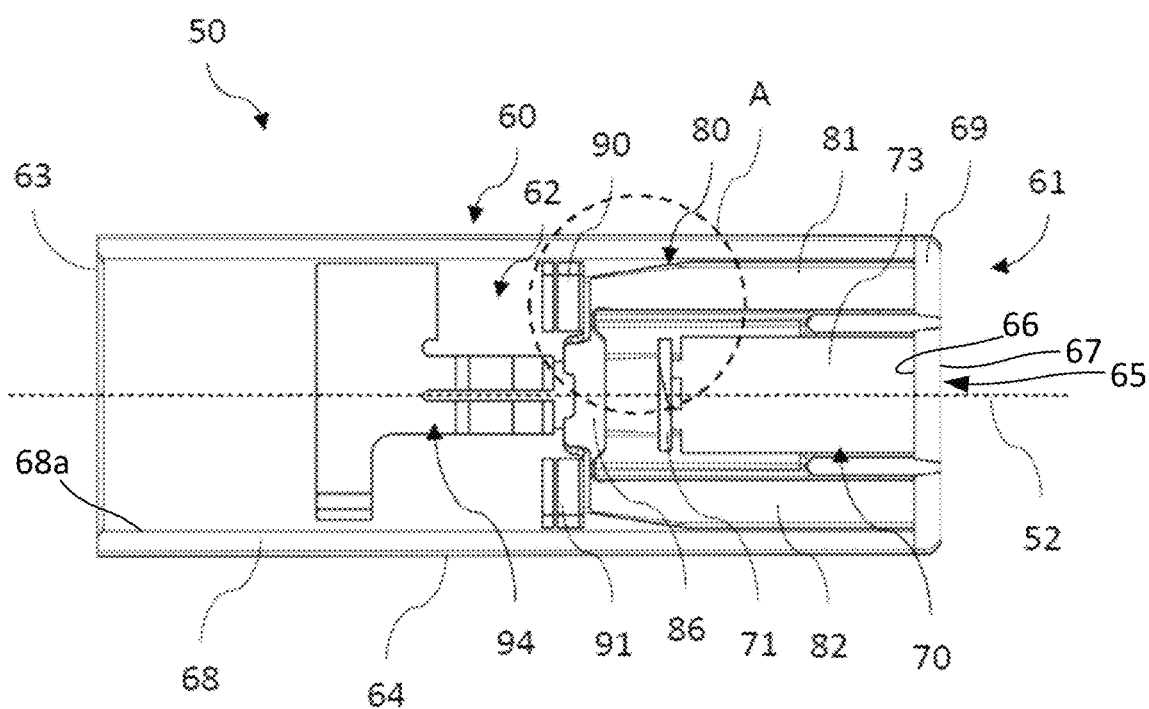
FIG. 4b is a schematic side cross-sectional illustration of the distal tip along the A-A line of FIG. 3 and illustrates detail view A.

Turning to FIGS. 3 and 4a-4b, the endoscope tip part 50 can be seen in greater detail without the bending section 40. FIG. 3 also shows lines A-A and B-B identifying cross-sections illustrated in FIGS. 4a, 4b, and 5. The tip part 50 comprises an exterior surface 51 facing the exterior of the tip part 50, and a tip housing 60 having an exterior surface 64, the tip housing 60 comprising a cylindrical-shell shaped circumferential wall 68 extending circumferentially around a longitudinal axis 52 and surrounding an interior space 62 as best seen in FIGS. 4a-4b. The circumferential wall 68 is closed at a distal end of the tip housing 60 by a distal end wall 69 and has a proximal opening 63, which provides the only access to the interior space 62, at the opposite end of the tip housing 60. The circumferential wall 68 has an interior surface 68a. As described below, in some embodiments a guide light component is sized and shaped to fit closely with the interior surface 68a defining a narrow gap which limits the possibiliy of adhesive flowing from a proximal to a distal compartment. The tip housing 60 comprises an opaque, or first, portion and a transparent, or second, portion including a window 65 arranged in or adjacent the distal end wall 69. Optionally, a couple of parallel, opaque, internally extending walls extend toward the window, which in a two-step molding process is molded around their distal ends. The parallel walls provide a light shield for the imaging subassembly 70. The window 65 has an interior surface 66 facing the sealed interior space 62 and an exterior surface 67 forming part of the exterior surface 51 of the tip housing 60. The exterior surface 67 of the window 65 and the distal ends of the parallel walls form a distal end face 61 (shown in FIG. 2). The tip housing may be manufactured by two-shot injection moulding processes so that the transparent portion 65 is formed by a transparent polymer material shot of the two shot injection moulding process and the opaque portion is formed by an opaque polymer material shot of the two shot injection moulding process so that the tip housing 60 is formed as a monolithic polymer piece. The tip part 50 further comprises a separately formed plug or proximal wall (not shown) arranged in and sealing the proximal opening 63 via an adhesive, thereby fully liquid- and gas-sealing the air-filled interior space 62. The tip housing may be manufactured by adhering the transparent portion 65 to the opaque portion.

Figure 11:
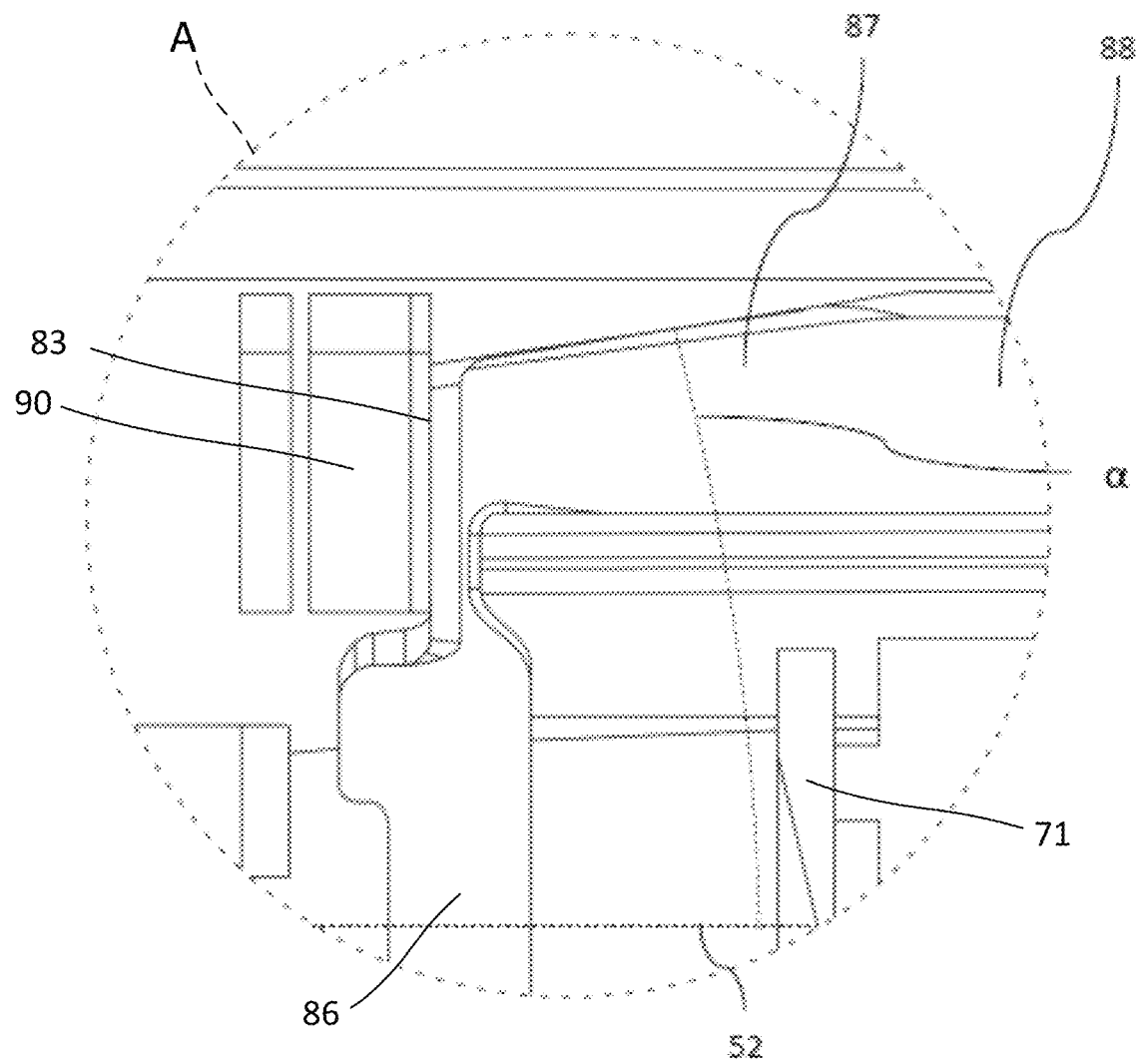
FIG. 11 is an enlarged view of detail view A as shown in FIG. 4b and illustrates transition portion of the light guide defining the taper angle α.

As best seen in FIGS. 4a-4b, the tip part 50 comprises an imaging subassembly 70, a first embodiment of a guide light component 80, a first and a second light source 90, 91, and an electrical circuit 94 mounted on a frame part (not shown). An enlarged view of detail view A of FIG. 4b is shown in FIG. 11.

The imaging subassembly 70 includes a lens barrel 73 and an image sensor 71 viewing in an optical direction 72 (shown in FIG. 6a) through the lens barrel 73 and out through the window 65 of the tip housing 60. The lens barrel 73 comprises several lenses enclosed in a barrel. The lenses optimise the view of the image sensor 71 and the barrel forms an optical barrier preventing stray light from entering the image sensor 71.

The first embodiment of the light guide component 80 includes a first and a second light guide 81, 82 spaced apart by a gap and extending in parallel along a respective straight longitudinal central center line. Each light guide has a proximal end, a distal end opposite of the proximal end, a light entry surface 83 at the proximal end, a light exit surface 84 at the distal end, and a circumferential surface 85 extending from the light entry surface 83 to the light exit surface 84 around the respective longitudinal central center line. The light entry surfaces 83 of the first and second light guides 80, 81 are planar and parallel, and the light exit surfaces 84 of the first and second light guides 80, 81 are planar and parallel. The circumferential surface 85 defines a polymer-air interface between the light guide component 80 and the interior space 62. The light guide component 80 further includes a crossmember 86 extending transversely from the proximal end of the first light guide 81 to the proximal end of the second light guide 82 over the gap between the light guides 81, 82. The light guide component 80 is monolithically formed of a rigid and transparent polymer material with a refractive index that is higher than the refractive index of air. This ensures that the critical angle for total internal reflection of light incident on the circumferential surface 85 of each light guide 81, 82 is also increased and thus increases the ability of the light guides 81, 82 to propagate light from the respective light entry surface 83 to the respective light exit surface 84 and thereby minimising light loss through the circumferential surfaces 85.

The tip part 50 further comprises a first and a second light source 90, 91 each formed of a single phosphor-based light-emitting diode for emitting substantially white light. Each light source 90, 91 comprises a single semiconductor die (not shown) for emitting light surrounded by an epoxy-based cover with an exterior surface forming a light-emitting surface 92. The light-emitting surface 92 of each light source 90, 91 is adhered to the light entry surface 83 of the respective light guide 80, 81 by an adhesive so that light emitted by each light source 90, 91 is propagated by the respective light guide 80, 81 out through the window 65 to provide illumination for the image sensor 71. Alternatively, the light source could be the distal end of an optical fibre transporting light from an LED arranged in the handle of the endoscope.

Figure 5:
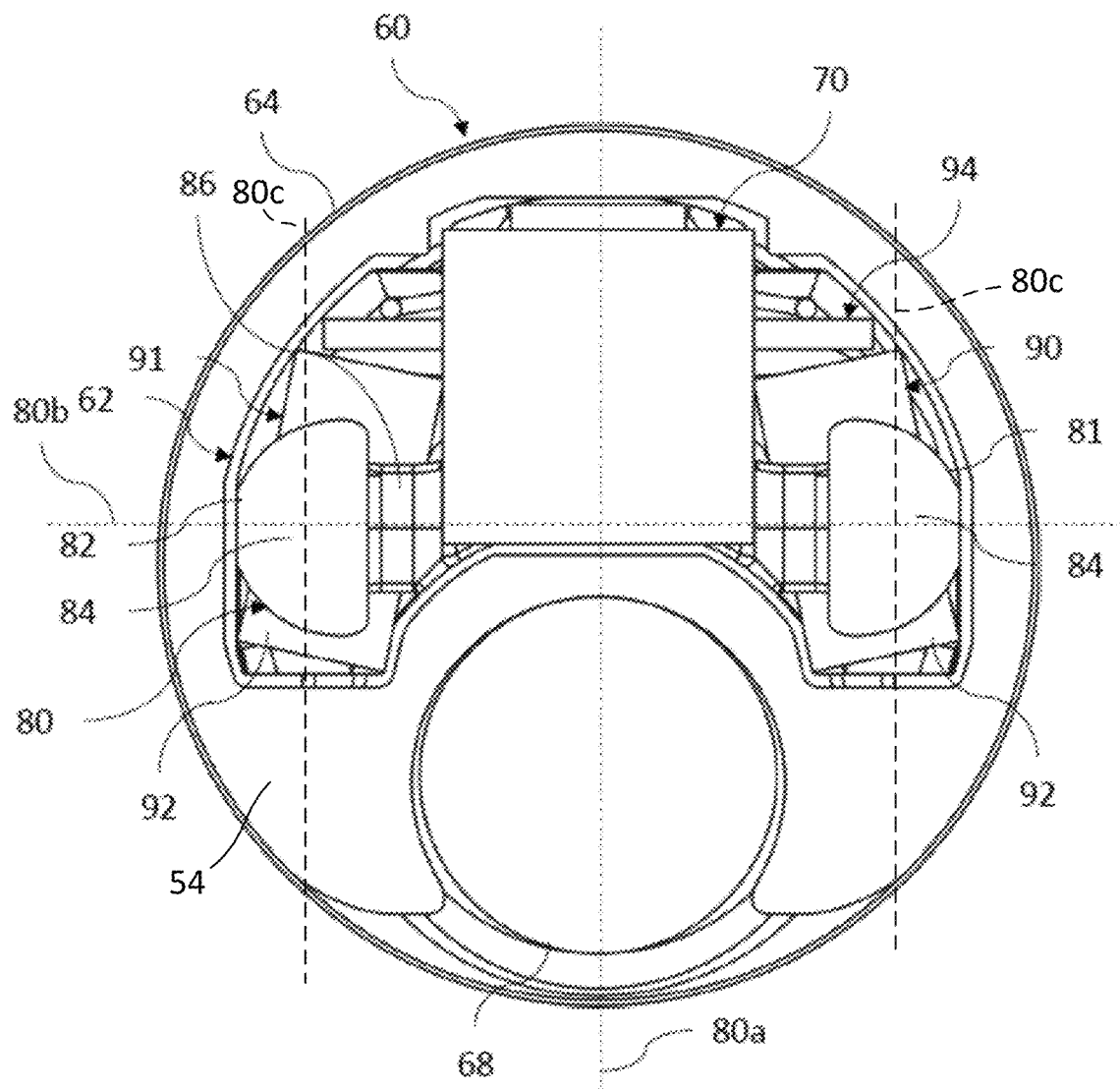
FIG. 5 is a schematic side cross-sectional illustration of the distal tip along the B-B line of FIG. 3, FIGS. 6a-6b are schematic illustrations of the distal tip of FIG. 3 without the tip housing in a perspective and side view, respectively.

As best seen in FIG. 5, in their intended position the first and the second light sources 90, 91 are partially overlapping the imaging subassembly 70, in particular the lens barrel 73, when viewed in a cross-section normal to the longitudinal axis 52. When accounting for manufacturing and assembly variance, the overlap of the light sources 90, 91 with the imaging subassembly 70 is significant in a large proportion of tip parts. An overlap gap Go is shown and described in FIG. 8. The allowance for overlap enables use of larger light emitting diodes (LEDs) and also use of LEDs with different shapes chosen to maximize lighting and minimize the size of tip part. A transverse wall 54 is molded along cross-section B-B within the housing circumpherential wall. The transverse wall 54 has an opening through which the imaging subassembly 70 is introduced in the the distal compartment.

The light guide component crossmember is positioned proximally of the image sensor and overlapping the image sensor in a longitudinal direction. In this instance, "overlapping" denotes that the crossmember traverses a longitudinal projection of the image sensor, e.g. it falls within a "shadow" cast by the image sensor in the longitudinal direction.

The light guides 81, 82 have mutual reflection symmetry in a first plane 80a extending equidistantly between the light guides 81, 82 and does not intersect the light guides 81, 82. The first plane 80a comprises the longitudinal direction 52 of the tip part 50. Each light guide 81, 82 has individual reflection symmetry in a second plane 80b comprising the longitudinal central center line of each light guide 81, 82 and being perpendicular to the first plane 80a. Each light guide is asymmetric in a respective third plane 80c. The third plane 80c is perpendicular to the second plane 80b and parallel to the first plane 80a and comprises the longitudinal central center line of the respective light guide 81, 82. This allows more compact packing of the elements of the tip housing.

Figure 6A:
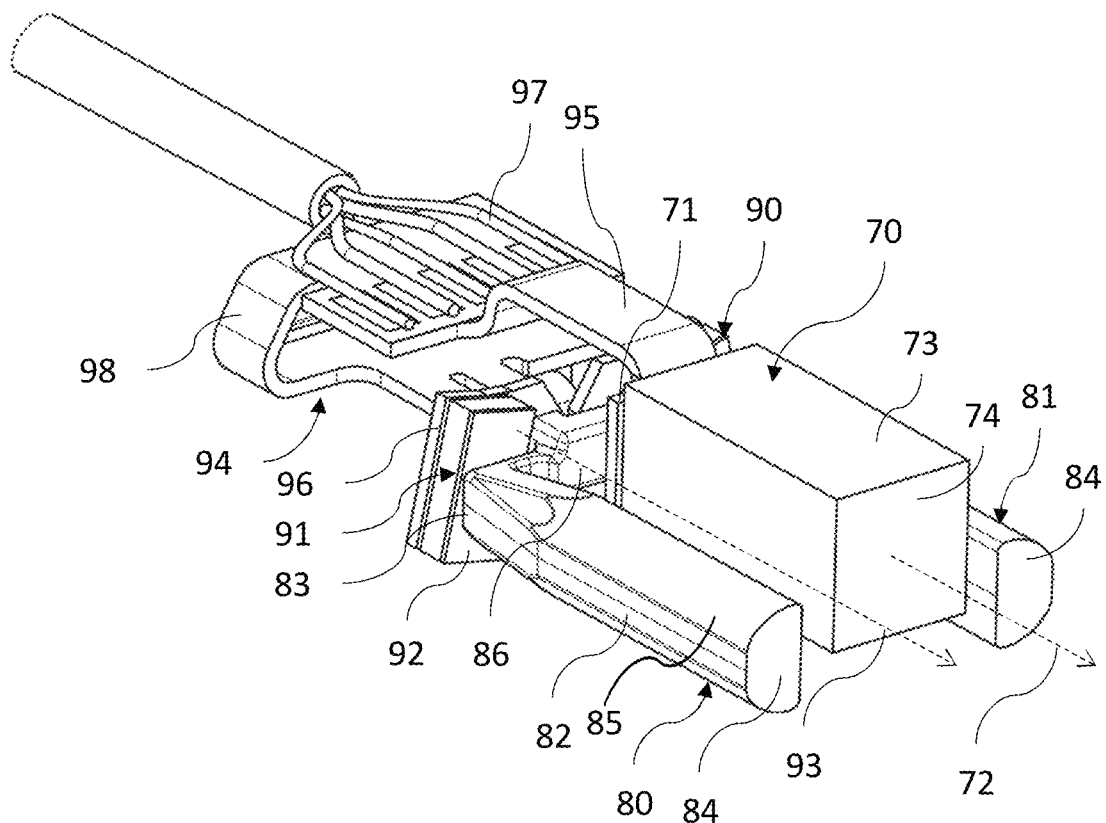
Figure 6B:
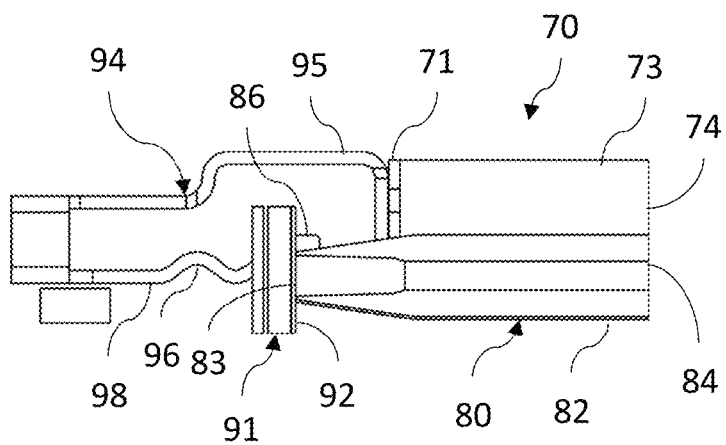

Turning to FIGS. 6A-6B showing the tip part 50 without the tip housing 60, the tip part 50 further comprises an electrical circuit 94 provided on a flexible circuit board (FPC). The electrical circuit 94 comprises a folded main circuit portion 98, a first circuit portion 95 in electrical communication with the image sensor 71 and the main circuit portion 98, and a second circuit portion 96 in electrical communication with the first and second light source 90, 91 and the main circuit portion 98. The electrical circuit 94 is configured for transmitting an image signal generated by the image sensor 71 indicative of the view in the optical direction 72 to a circuit (not shown) of the handle 20 of the endoscope 1 via several cables 97 connected to the main circuit portion 98 as best seen in FIG. 6a. It should be understood that as used herein the term "cable" denotes an insulated wire and the word "cables" denotes a plurality of insulated wires, which may or may not be enclosed in a sheath. The first and the second circuit portions 95, 96 are flexible circuit structures and comprise a slight bend which allow, prior to fixing in the tip housing 60, the imaging subassembly 70 and light sources 90, 91 to move along the longitudinal direction 52, which in this case coincides with the optical direction 72, relative to each other via the flexing of first and second circuit portions 95, 96. The electrical circuit 94 is positioned distally relative to the plug (not shown) and is accommodated in the sealed interior space of the tip housing 60.

A surface normal 93 of each light-emitting surface 92 is preferably oriented in parallel to the optical direction 72 of the image sensor 71 so that light is emitted from the light sources 90, 91 in the same direction as the view of the image sensor 71. The light guide component 80 is arranged so that the imaging subassembly 70 occupies the gap between the light guides 81, 82 and so that the light sources 90, 91 are positioned proximally, i.e. behind, relative to the image sensor 71. This allows a more compact configuration of the imaging subassembly 70 and the light sources 90, 91.

Figure 7A:
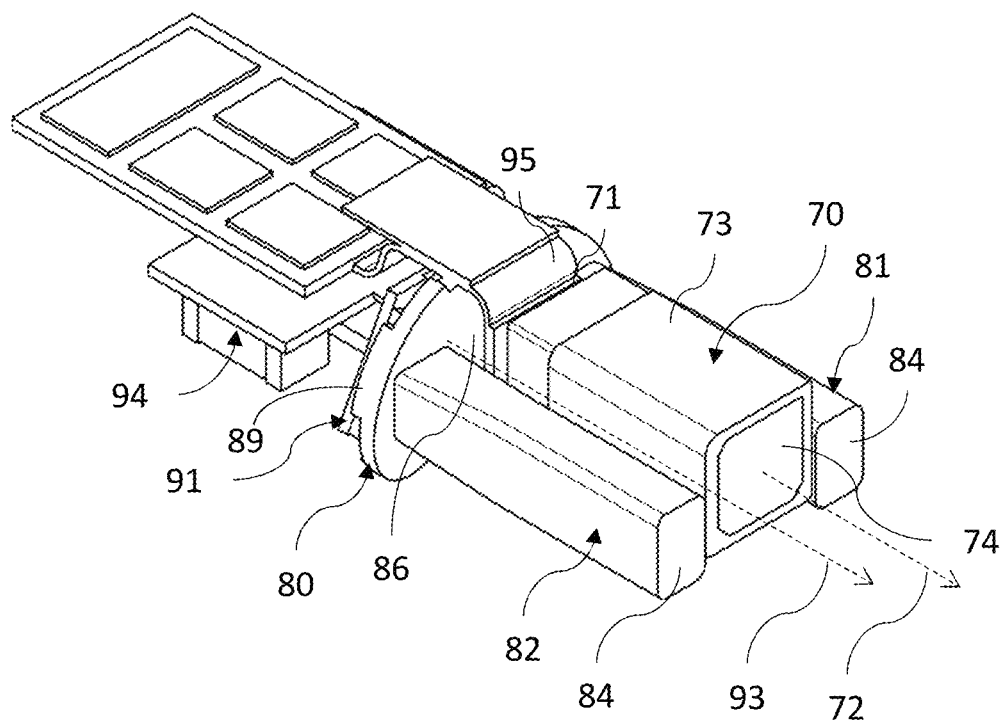
FIGS. 7a-7b are schematic illustrations of a second embodiment of a distal tip without the tip housing in a distal and proximal perspective view, respectively.
Figure 7B:
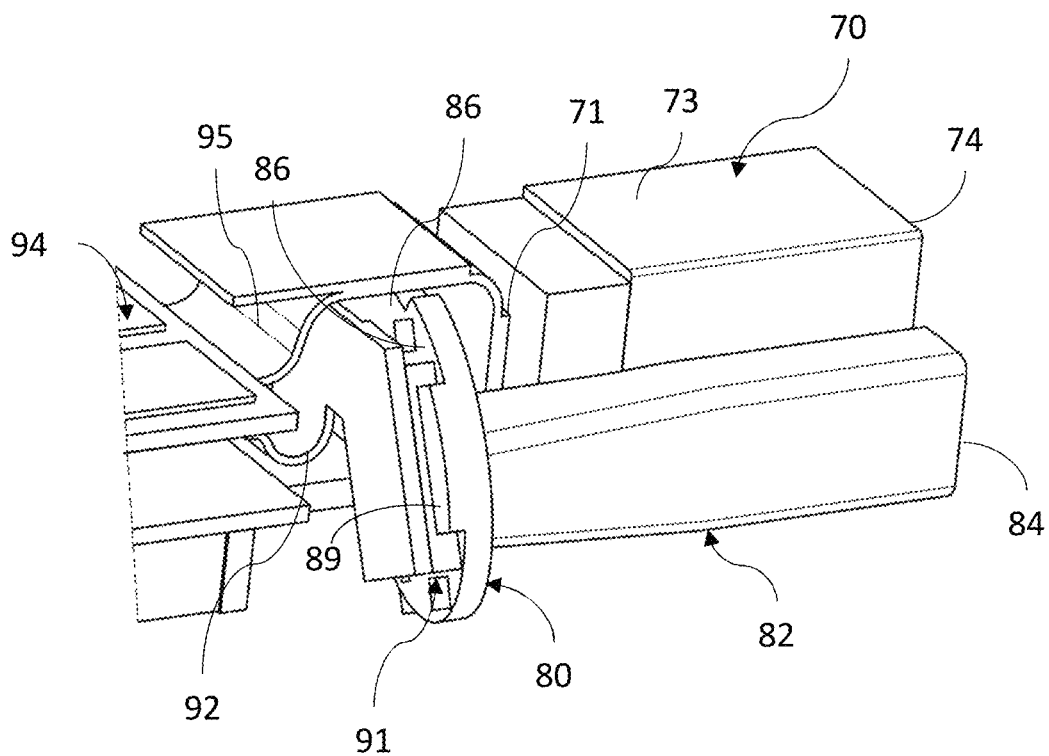

Turning to FIG. 7a-7b, a tip part 50 with a second embodiment of a light guide component 80 is shown without a tip housing and without cables. This second embodiment differs from the previously shown light guide component in that the light guide component comprises at least one rail 89 at each light entry surface 83, in that the crossmember 86 is plate shaped, and in that each light guide 81, 82 is not asymmetric in a corresponding third plane 80c. As best seen in FIG. 7b, the rails 89 partially surround the respective light entry surface 83 and are configured to retain and define a seat for the respective light source 90, 91 adhered to the respective light entry surface. Two or more rails may be provided to create a frame around the seat, such that during assembly the light source can easily and quickly be adhered to the light guide component 80. The plate-shaped crossmember 86 provides a barrier with only a narrow gap between the crossmember 86 and the interior surface 68a of the tip housing. Thus, the crossmember 86 prevents sealing adhesive applied proximal to the crossmember 86 from passing the crossmember 86, which could negatively affect the function of the light guides 81, 82. The internal space proximal of the crossmember 86 can be referred to as a proximal compartment and the distal space can be referred to as the distal compartment. The light guides 81, 82 are in the distal compartment. The narrow gap, shown as gap Ga (e.g. adhesive gap) in FIG. 8, extends along lateral arcuate peripheries of the plate-shaped crossmember 86, best seen in FIG. 7a. By plate-shaped is meant that the transverse surface of crossmember 86 extends beyond the surface area of the light receiving surfaces of the light guides, the additional surface providing an adhesive barrier by the defining, together with surface 68a, the narrow gap Ga, and also providing a support on which to place the rails. What constitutes a "narrow" gap depends on the viscosity of the adhesive. Denser adhesives permit wider gaps and vice versa. The gap size can be determined experimentally by placing sealing adhesive in the proximal compartment and observing whether the sealing adhesive passes through the gap to affect the function of the light guides. Sealing adhesive can be used after assembly to secure the circuit board and imaging subassembly 70 in place.

Figure 8:
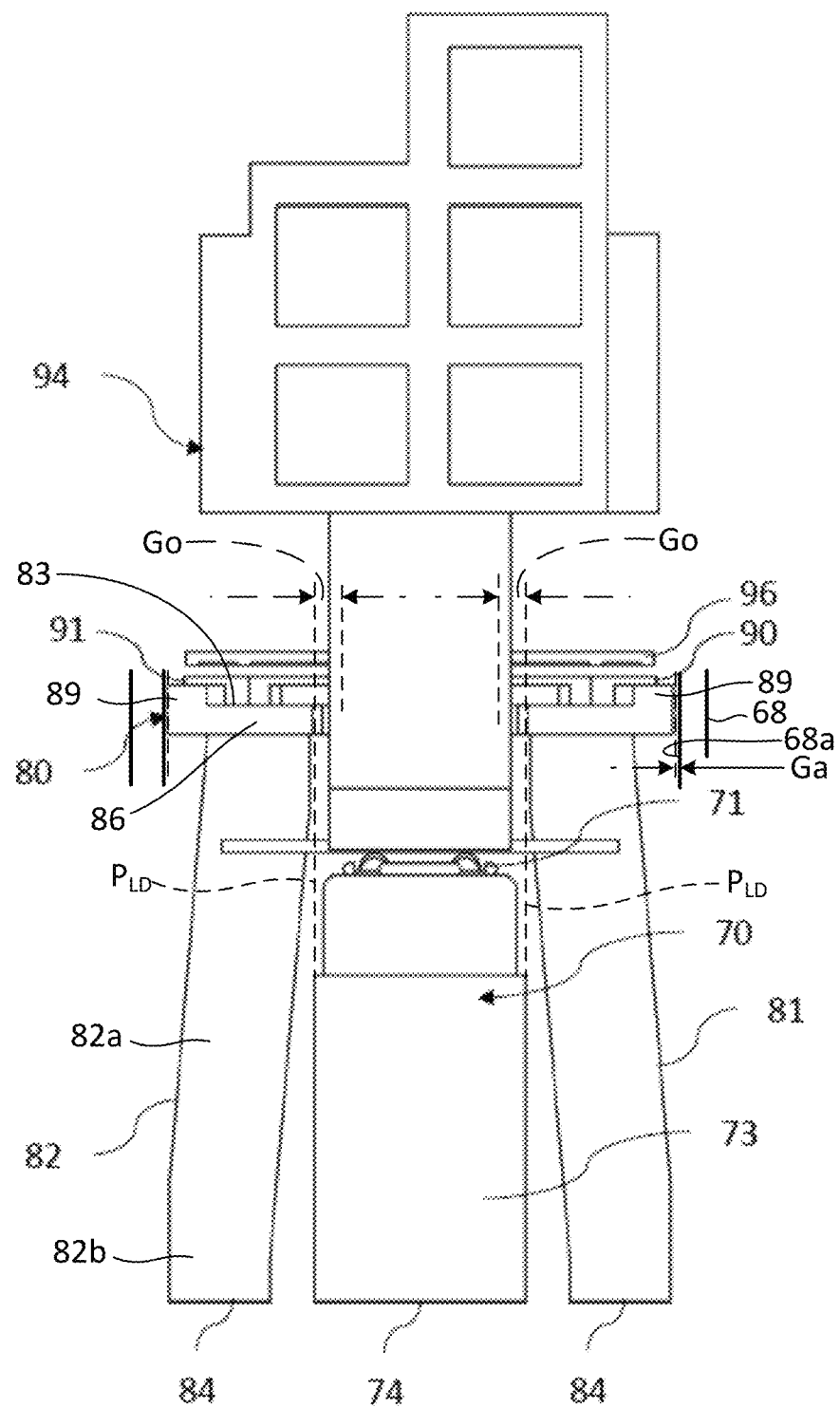
FIG. 8 is a schematic top view of a third embodiment of a distal tip without the tip housing.

Turning to FIG. 8, a tip part 50 with a third embodiment of a light guide component 80 is shown without a tip housing and without cables. This third embodiment differs from the second embodiment in that the longitudinal central center line is not straight but rather follows an angled course and comprises an initial outwardly angled part 82*a* at the light entry surface and a final straight part 82*b*. An overlap gap Go is shown. Similar overlap gaps Go can be present in the first and second embodiments. A pair of dashed lines $P_{LD}$ represent the longitudinal projections of the surfaces of the imaging subassembly 70 and these dashed lines pass through the light sources 90, 91, the gaps Go representing the amount of overlap. The inner-most aspect of the light sources 90, 91, also represented by dashed lines, may be beneath the circuit 94 board and thus not visible in FIG. 8. The allowance for overlap enables use of larger light emitting diodes (LEDs) and also use of LEDs with different shapes chosen to maximize lighting and minimize the size of tip part. The narrow gap Ga is shown between the lateral arcuate periphery(ies) of the plate-shaped crossmember 86, best seen in FIG. 7*a*, and the internal surface 68*a* of circumpherential wall 68.

Assembly of the tip part 50 is performed as follows. The tip housing 60, the plug (not shown), the light guide component 80, and the electrical circuit 94 are provided as separately manufactured parts. The tip housing 60, the plug and the light guide component 80 are injection-moulded polymer parts. The electrical circuit 94 are mounted on a frame part (not shown) and has the imaging subassembly 70 and the light sources 90, 91 pre-mounted on the respective circuit portions 95, 96. The light guide component 80 can be any one of the three described embodiments.

The light-emitting surface 92 of first light source 90 is then adhered directly to the light entry surface 83 of the first light guide 81 and the light-emitting surface 92 of the second light source 91 is adhered directly to the light entry surface 83 of the second light guide 82. This ensures that light emitted from the light sources is received by the respective light guide and transmitted out via the respective light exit surface 84, and that the electrical circuit 94, imaging subassembly 70, the light sources 90, 91, and the light guide component 80 can be handled as a main subassembly, e.g. as shown in FIGS. 4*a*-4*b*, FIGS. 6*a*-6*b*, or FIG. 8.

The main subassembly is then positioned in a jig (not shown) that allows only relative translational adjustment of the light guide component 80 relative to the imaging subassembly 70. The distal end 74 of the lens barrel 73 is then adjusted to a predetermined position relative to the light exit surfaces 84 of the light guide component 80 via flexing of the first and second circuit portions 95, 96. This predetermined position corresponds to the desired position of these components in the tip housing 60 and is in this case that the distal end 74 of the lens barrel 73 is positioned in the same plane as the light exit surfaces 84, as can best be seen in FIGS. 6*b* and 8. The light guide component 80 and the imaging subassembly 70 are then fixed to the frame part to fix their relative position.

This main subassembly is then inserted through the proximal opening 63 of the tip housing 60 into the interior space 62 so that the optical direction 72 of the image sensor 71 extends through the window 65, and so that the light exit surface 84 of the first and second light guides 81, 82 is oriented towards the interior surface 66 of the window 65. The main subassembly is pushed into the interior space 62 until the light exit surfaces 84 and the distal end 74 of the lens barrel 73 abut the interior surface 66 of the window 65 simultaneously due to the prior relative adjustment. The main subassembly is then adhered to the interior surface of the tip housing 60.

The plug (not shown) is then inserted into and closes off the proximal opening 63 while allowing the cables 97 to pass therethrough to the handle 20. An adhesive is applied between the plug and an interior housing surface to fluid and gas seal the interior space 62. The tip part 50 can then be assembled with the bending section 40, the insertion tube 30, and the handle 20, to form the endoscope shown in FIG. 1.

Figure 9:
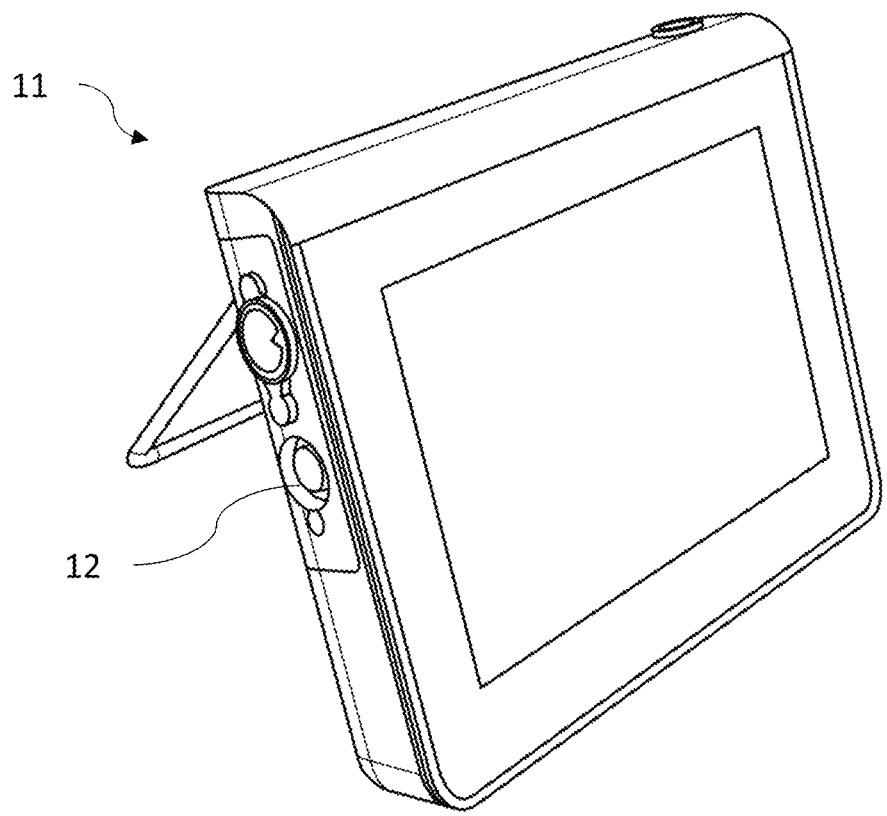
FIG. 9 is a schematic perspective illustration of a monitor connectable to the endoscope of FIG. 1.

In FIG. 9, a monitor 11 is shown. The monitor 11 comprises a cable socket 12 to which a monitor cable 13 of the endoscope 1 shown in FIG. 1 can be connected to establish signal communication between the image sensor of the endoscope 1 and the monitor 11 via a circuit of the handle 20 connected to the electrical circuit 94 of the housing 60 of the tip part 50 via the cables 97. The monitor 11 display images and/or video captured by the image sensor of the endoscope 1, thus allowing an operator to see through the image sensor of the endoscope 1.

Figure 10A:
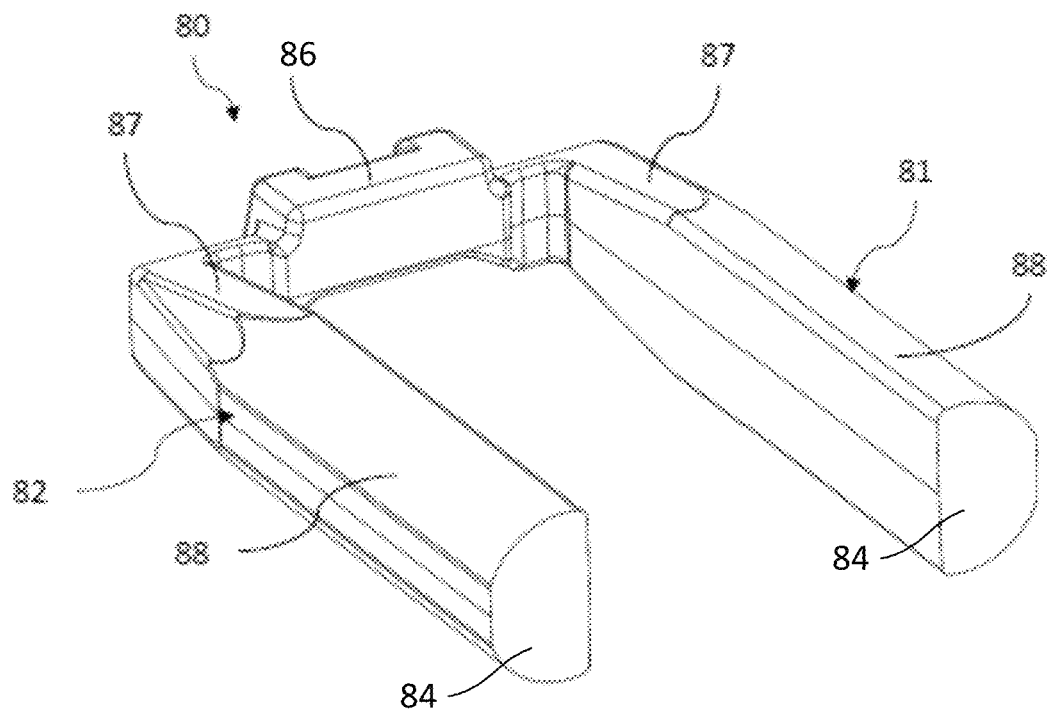
FIG. 10a is a schematic perspective illustration of the light guide component alone.
Figure 10B:
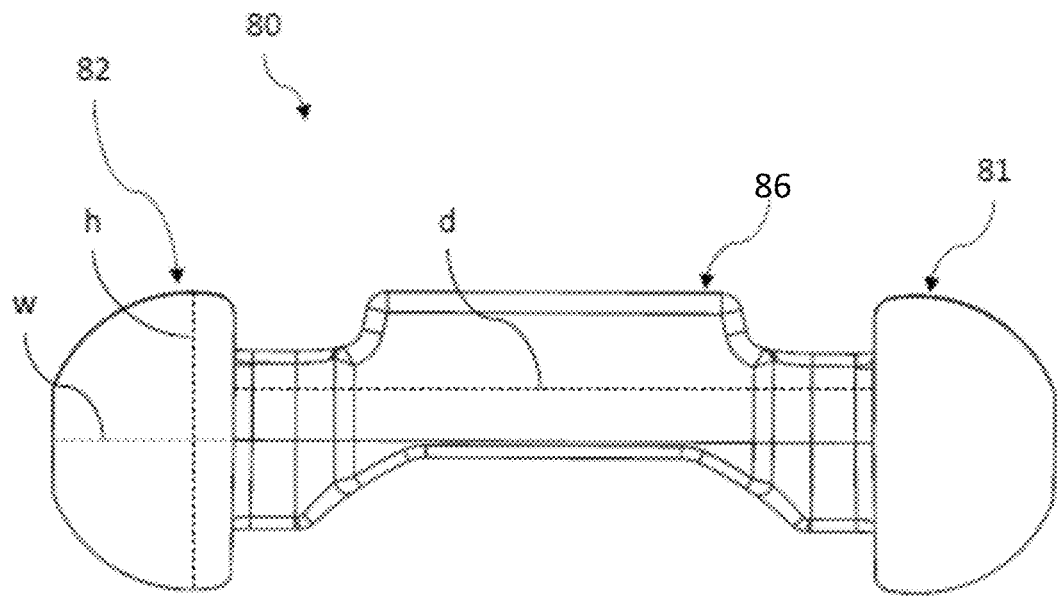
FIG. 10b is a schematic cross-sectional illustration of the light guide component in a plane perpendicular to the longitudinal axis of the distal tip part.

As best seen in FIGS. 10*a*-10*b*, each light guide 81, 82 comprises a tapering transition portion 87 including the respective light entry surface 83 and a straight portion 88 directly extending from the transition portion 87 to the respective light exit surface 84. As shown in FIG. 10*b*, the straight portion 88 of each light guide 81, 82 has a width w and a height h. Further, the light guides 81, 82 are spaced apart transversely to the longitudinal axis 52 by a distance d. The width w is in the range of 0.35-0.55 mm, preferably in the range of 0.4-0.5 mm. The height h is in the range of 0.6-0.8 mm, preferably in the range of 0.65-0.75 mm. The distance d is in the range of 1.3-1.8 mm, preferably in the range of 1.4-1.7.

FIG. 11 is an enlarged view of detail view A of FIG. 4*b*. As can be seen on FIG. 11, the transition portion 87 of each light guide 81, 82 tapers from the respective light entry surface 83 to the respective straight portion 88 with a taper angle α with respect to the longitudinal axis 52. The taper angle α is in the range 1-12 degrees, preferably 5-10 degrees, more preferably 7-10 degrees.

The following items are examples of various embodiments disclosed above:

Item 1. An endoscope tip part for an endoscope for visually inspecting inaccessible places, such as human body cavities, the endoscope tip part having an exterior surface and extending along a longitudinal axis and comprising:

a tip housing extending along the longitudinal axis and at least partially enclosing a sealed interior space, the tip housing including:

an exterior housing surface for forming a first part of the exterior surface of the endoscope tip part, and a transparent portion, such as a window or a front lens, having an interior surface facing the sealed interior space of the endoscope tip part and an exterior surface forming a second part of the exterior surface of the endoscope tip part;

an imaging subassembly including an image sensor viewing in an optical direction through the transparent portion of the tip housing;

a light guide component comprising a first light guide having a light entry surface and a light exit surface, the first light guide being configured for propagating light received through the light entry surface out through the light exit surface and the transparent portion of the tip housing;

a first light source being configured to emit light in a central illumination direction to be received by the light entry surface of the first light guide; and an electrical circuit comprising a first circuit portion in electrical communication with the image sensor, the electrical circuit being configured for transmitting an image signal generated by the image sensor indicative of the view in the optical direction;

wherein the first light source, the image sensor, and the electrical circuit are accommodated in the sealed interior space of the tip housing, wherein the first light source is attached to the light guide component and preferably positioned proximally relative to the image sensor.

Item 2. An endoscope tip part according to item 1, wherein the light guide component comprises a second light guide having a light entry surface and a light exit surface, the second light guide being configured for propagating light received through the light entry surface out through the light exit surface and the transparent portion of the tip housing, wherein the endoscope tip part comprises a second light source having a light-emitting surface and being configured to emit light from the light-emitting surface in a central illumination direction to be received by the light entry surface of the second light guide, wherein the second light source is attached to the light guide component and preferably positioned proximally relative to the image sensor, and wherein the first and second light guides extend side-by-side on opposite sides of the imaging subassembly.

Item 3. An endoscope tip part according to any one of the previous items, wherein the light guide component is formed separately from the tip housing, and wherein the first light guide exit and/or the second light guide exit is/are oriented towards the interior surface of the transparent portion.

Item 4. An endoscope tip part according to any one of the previous items, wherein the tip housing comprises a distal end face and a proximal opening providing access to the sealed interior space, wherein the distal end face is positioned opposite the proximal opening, and wherein the distal end face comprises at least part of the exterior surface of the transparent portion.

Item 5. An endoscope tip part according to any one of the previous items, wherein the first and/or the second light source(s) is/are at least partially overlapping the imaging subassembly when viewed in a cross-section perpendicular to the longitudinal axis.

Item 6. An endoscope tip part according to any one of the previous items, wherein the first and/or the second circuit portion(s) is/are flexible circuit structures.

Item 7. An endoscope tip part according to any one of the previous items, wherein the first and/or the second light guide consist(s) essentially of a transparent material with a first refractive index, and wherein the light-emitting surface of the light source(s) is/are adhered to the light entry surface of the respective light guide by an adhesive.

Item 8. A light guide component for an endoscope tip part, the light guide component comprising:

a first and a second light guide being spaced apart by a gap and extending along a respective longitudinal centre line, wherein each light guide has a proximal end, a distal end, a light entry surface at the proximal end, a light exit surface at the distal end, and a circumferential surface extending from the light entry surface to the light exit surface around the respective longitudinal centre line, and a crossmember extending transversely from the first light guide to the second light guide so as to form a unitary rigid light guide component, wherein the light guides are configured for propagating light received through the respective light entry surface out through the respective light exit surface.

Item 9. A light guide component according to item 8, wherein the crossmember extends transversely from the proximal end of the first light guide to the proximal end of the second light guide.

Item 10. A light guide component according to any one of the items 8-9, wherein the light guide component is formed monolithically.

Item 11. A light guide component according to any one of the items 8-10, wherein the light entry surfaces of the first and second light guides are planar, and/or wherein light exit surfaces of the first and second light guides are planar.

Item 12. An endoscope tip part according to any one of the items 1-7, wherein the light guide component is a light guide component according to any one of items 8-11.

Item 13. An endoscope for visually inspecting inaccessible places such as human body cavities, comprising:

a handle for gripping by an operator and comprising a control device;

an endoscope tip part according to any one of the items 1-7 or item 12;

an insertion tube for insertion into a patient, the insertion tube extending from the handle to the endoscope tip part and comprising a bending section;

one or more cables running through the insertion tube and electrically connecting the electrical circuit of the endoscope tip part with the handle; and at least one steering wire connecting the handle with a distal end of the bending section so that manipulation of the control device causes bending of the bending section.

Item 14. An endoscope system for visually inspecting inaccessible places, such as human body cavities, the endoscope system comprising a monitor, and an endoscope according to item 13 or an endoscope comprising an endoscope tip part according to any one of items 1-7 or 12, wherein the endoscope is connectable to the monitor, and the monitor is configured for displaying an image captured by the image sensor of the endoscope tip part.

Item 15. A method for assembling an endoscope tip part, the endoscope tip part extending along a longitudinal axis, the method comprising the steps of:

providing:
a housing extending along the longitudinal axis and at least partially enclosing an interior space, the tip housing including:
a proximal opening providing access to the interior space,
an exterior housing surface for forming an exterior surface of the endoscope tip part, and
a transparent portion, such as a window or a front lens, having an interior surface and an exterior surface, the interior surface facing the interior space of the endoscope tip part and the exterior surface facing the exterior of the endoscope tip part,
an imaging subassembly including an image sensor viewing in an optical direction,
a light guide component comprising a first light guide including a proximal end, a distal end, a light entry surface at the proximal end, a light exit surface at the distal end, and a circumferential surface extending from the light entry surface to the light exit surface around the respective longitudinal centre line, the first light guide being configured for propagating light received through the light entry surface out through the light exit surface, a first light source having a light-emitting surface and being configured to emit light from the light-emitting surface in a central illumination direction, and an electrical circuit comprising a first circuit portion in electrical communication with the image sensor and a second circuit portion in electrical communication with the light source(s), the electrical circuit being configured for transmitting an image signal generated by image sensor indicative of the view in the optical direction, wherein at least one of the first and second circuit portions is flexible so the image sensor and light source(s) are movable relative to each other;

attaching the first light source to the light guide component, so that light emitted by the first light source is received by the light entry surface of the first light guide, and so that the imaging subassembly, the light guide component, and the electrical circuit form a main subassembly;

inserting the main subassembly through the proximal opening of the tip housing into the interior space so that the optical direction of the image sensor extends through the transparent portion, and so that a surface normal of the light exit surface of the first light guide is at least partially oriented towards the interior surface of the transparent portion;

fixing the main subassembly to the tip housing and sealing the proximal opening to seal the interior space.

Item 16. A method according to item 15, wherein the light guide component is provided according to any one of items 8-11.

Item 17. A method according to any one of items 15-16, further comprising a step of:

arranging the main subassembly in a jig, adjusting the light guide component relative to the imaging subassembly to a predetermined relative position along the longitudinal direction via flexing of the first and/or second circuit portion, and subsequently fixing the light guide component relative to the imaging subassembly, wherein the step of inserting the main subassembly comprises inserting the main subassembly along the longitudinal direction until a distal end of the imaging subassembly abuts an interior distal portion of the tip housing, and until a distal end of the light guide component abuts an interior distal portion of the tip housing.

LIST OF REFERENCES

The following is a list of reference numerals used throughout this disclosure. In case of any doubt, the reference numerals of the following list apply.

1 endoscope
11 monitor
12 cable socket
13 monitor cable
20 handle
21 control lever
22 handle housing
24a steering wire
24b steering wire
30 insertion tube
31 exterior tubular surface
32 working channel
40 bending section
41 proximal end
42 sleeve
43 segment
44 hinge
50 tip part
51 exterior surface
52 longitudinal axis
54 wall
60 housing
61 distal end face
62 interior space
63 proximal opening
64 exterior housing surface
65 window
66 interior window surface
67 exterior window surface
68 circumferential wall
68a circumferential wall internal surface
69 distal end wall
70 imaging subassembly
71 image sensor
72 optical direction
73 lens barrel
74 distal end
80 light guide component
80a first plane
80b second plane
80c third plane 81 first light guide
82 second light guide
83 light entry surface
84 light exit surface
85 circumferential surface
86 crossmember
87 transition portion
88 straight portion
89 rail
α taper angle
90 first light source
91 second light source
92 light-emitting surface
93 central illumination direction
94 electrical circuit
95 first circuit portion
96 second circuit portion
97 cable
98 main circuit portion

The invention claimed is:

1. An endoscope tip part for an endoscope, the endoscope tip part comprising:

a housing at least partially enclosing an interior space, the housing including a transparent portion having an interior surface facing the interior space and a proximal opening;

an imaging subassembly including an image sensor viewing in an optical direction through the transparent portion of the housing;

a single-piece light guide component comprising a crossmember, a first light guide and a second light guide, the first light guide having a light entry surface and a light exit surface, the second light guide having a light entry surface and a light exit surface, the light entry surface of the first light guide and the light entry surface of the second light guide positioned at opposite ends of the cross-member and spaced apart by a gap, the crossmember positioned proximally of the image sensor and overlapping the image sensor in a longitudinal direction, the first light guide and the second light guide being connected to, and extending distally from, the cross-member;
a first light emitting diode attached to the light guide component adjacent the light entry surface of the first light guide and proximally relative to the image sensor;
a second light emitting diode attached to the light guide component adjacent the light entry surface of the second light guide and proximally relative to the image sensor,
wherein the first light emitting diode, the second light emitting diode and the image sensor are accommodated in the interior space of the housing distally of the proximal opening.

2. The endoscope tip part of claim 1, wherein the first light guide and the second light guide extend side-by-side on opposite sides of the imaging subassembly.

3. The endoscope tip part of claim 2, wherein the first light emitting diode and the second light emitting diode at least partially overlap the imaging subassembly when viewed along the longitudinal direction.

4. The endoscope tip part of claim 1, wherein the first light emitting surface of the first light emitting diode is adhered by an adhesive to the light entry surface of the first light guide.

5. The endoscope tip part of claim 4, wherein the light exit surface of the first light guide is detached from the transparent portion.

6. The endoscope tip part of claim 1, further comprising an electrical circuit and cables connected to the electrical circuit, wherein the electrical circuit is entirely accommodated in the interior space of the tip housing, and wherein the cables extend proximally from the housing.

7. The endoscope tip part of claim 1, wherein the housing comprises a distal end face, wherein the distal end face is positioned opposite the proximal opening, and wherein the distal end face is comprised by a portion of the transparent portion and by a non-transparent portion.

8. The endoscope tip part of claim 1, wherein the first light guide and the second light guide extend side-by-side on opposite sides of the imaging subassembly.

9. The endoscope tip part of claim 8, wherein the light guide component is formed separately from the housing, and wherein the light exit surface of the first light guide and the light exit surface of the second light guide are oriented to emit light towards the interior surface of the transparent portion.

10. The endoscope tip part of claim 8, wherein the first light emitting diode and the second light emitting diode are at least partially overlapping the imaging subassembly when viewed in a cross-section perpendicular to the longitudinal axis.

11. The endoscope tip part of claim 8, wherein the first light guide and the second light guide consist essentially of a transparent material with a first refractive index, and wherein the light-emitting surface of the first light emitting diode and the second light emitting diode are adhered to the light entry surface of the first and the second light guide, respectively, by an adhesive.

12. The endoscope tip part of claim 1,
wherein each of the first and the second light guides extends along a respective longitudinal center line and a circumferential surface extending from the light entry surface to the light exit surface around the respective longitudinal center line,
wherein the first light guide and the second light guide are configured for propagating light received through the respective light entry surface out through the respective light exit surface,
wherein the imaging subassembly further comprises a lens barrel, and
wherein the longitudinal center lines of the first light guide and of the second light guide extend along respective sides of the lens barrel.

13. An endoscope comprising:
a handle for gripping by an operator and comprising a control device;
an endoscope tip part according to claim 1;
an insertion tube extending from the handle to the endoscope tip part and comprising a bending section;
one or more cables running through the insertion tube and electrically connecting an electrical circuit of the endoscope tip part with the handle; and
at least one steering wire connecting the handle with a distal end of the bending section so that manipulation of the control device causes bending of the bending section.

14. An endoscope system for visually inspecting inaccessible places, the endoscope system comprising:
a monitor; and
an endoscope according to claim 13,
wherein the endoscope is connectable to the monitor to display an image captured by the image sensor of the endoscope tip part.

15. A method for assembling the endoscope tip part of claim 1, the method comprising:
providing the housing;
providing the imaging subassembly;
providing the single-piece light guide component;
providing the first light emitting diode and the second light emitting diode;
attaching the first light emitting diode to the light guide component, so that light emitted by the first light emitting diode is received by the light entry surface of the first light guide, and so that the imaging subassembly, the light guide component, and the electrical circuit form a main subassembly;
inserting the main subassembly through the proximal opening of the housing into the interior space so that the optical direction of the image sensor extends through the transparent portion, and so that a surface normal of the light exit surface of the first light guide is at least partially oriented towards the interior surface of the transparent portion, with the first light emitting diode positioned proximally relative to the image sensor;
fixing the main subassembly to the housing; and
sealing the proximal opening to seal the interior space.

16. The method of claim 15, wherein the first light guide and the second light guide are sized and shaped to extend side-by-side on opposite sides of the imaging subassembly.

17. The method of claim 15, further comprising:
arranging the main subassembly in a jig, adjusting the light guide component relative to the imaging subassembly to a predetermined relative position along the longitudinal direction, and subsequently fixing the light guide component relative to the imaging subassembly,
wherein inserting the main subassembly comprises inserting the main subassembly along the longitudinal direction until a distal end of the imaging subassembly abuts an interior distal portion of the tip housing, and until a distal end of the light guide component abuts an interior distal portion of the housing.

18. The method of claim 15, further comprising:
arranging the main subassembly in a jig, adjusting the light guide component relative to the imaging subassembly to a predetermined relative position along the longitudinal direction, and subsequently fixing the light guide component relative to the imaging subassembly,
wherein inserting the main subassembly comprises inserting the main subassembly along the longitudinal direction until the light exit surface abuts the interior surface of the transparent portion of the housing.

19. The endoscope tip part of claim 1, wherein the light guide component comprises a rail partially surrounding the light entry surface.

20. The endoscope tip part of claim 19, wherein the cross-member is plate shaped.

21. The endoscope tip part of claim 19, wherein the light guide comprises an outwardly angled part and a straight, not outwardly angled, part.

22. The endoscope tip part of claim 1, wherein the light guide comprises an outwardly angled part and a straight, not outwardly angled, part.

* * * * *